(12) United States Patent
Bernard

(10) Patent No.: US 10,206,951 B2
(45) Date of Patent: Feb. 19, 2019

(54) METHODS OF TREATING MULTIPLE SCLEROSIS USING STRO-1+ AND TNAP+ MULTIPOTENTIAL CELLS

(75) Inventor: Claude Bernard, Clayton (AU)

(73) Assignee: MESOBLAST, INC., New York, NY (US)

( * ) Notice: Subject to any disclaimer, the term of this patent is extended or adjusted under 35 U.S.C. 154(b) by 0 days.

(21) Appl. No.: 14/123,758

(22) PCT Filed: Jun. 4, 2012

(86) PCT No.: PCT/AU2012/000626
§ 371 (c)(1),
(2), (4) Date: May 15, 2014

(87) PCT Pub. No.: WO2012/162754
PCT Pub. Date: Dec. 6, 2012

(65) Prior Publication Data
US 2014/0322276 A1  Oct. 30, 2014

Related U.S. Application Data

(60) Provisional application No. 61/493,073, filed on Jun. 3, 2011.

(51) Int. Cl.
| | | |
|---|---|---|
| *A61K 38/00* | (2006.01) | |
| *A01N 63/00* | (2006.01) | |
| *C12N 5/071* | (2010.01) | |
| *C12N 5/07* | (2010.01) | |
| *C12N 5/077* | (2010.01) | |
| *C12N 5/0775* | (2010.01) | |
| *C12N 5/0789* | (2010.01) | |
| *A61K 48/00* | (2006.01) | |
| *A61K 35/28* | (2015.01) | |
| *A61K 38/21* | (2006.01) | |
| *A61K 35/12* | (2015.01) | |

(52) U.S. Cl.
CPC ............ *A61K 35/28* (2013.01); *A61K 38/215* (2013.01); *C12N 5/0663* (2013.01); *A61K 2035/122* (2013.01)

(58) Field of Classification Search
CPC ................ A61K 2300/00; A61K 35/28; A61K 2035/122; A61K 35/50; A61K 35/51; A61K 35/545; A61K 5/0668; A61K 35/30; A61K 35/17; A61K 39/00; A61K 38/18; A61K 38/185; C07K 14/4713; G01N 33/56966; G01N 33/5073; G01N 33/6896; A61L 27/3834; C12N 5/0663; C12N 5/0607; C12N 506/1353; C12N 5/0619; C12N 5/0623; C12N 5/0647; C12N 5/0664; C12N 5/0669; C12N 2502/11358; C12N 2502/1382; C12N 2506/11; C12N 2506/1392; C12N 2502/1376; C12N 2502/1388; C12N 2502/1394; C12N 2506/1346; C12N 2502/1361; C12N 5/0606; C12N 5/0678; C12N 5/0692
See application file for complete search history.

(56) References Cited

U.S. PATENT DOCUMENTS

| | | | | |
|---|---|---|---|---|
| 8,017,112 B2 * | 9/2011 | Li et al. | ........................ | 424/93.7 |
| 8,367,405 B2 * | 2/2013 | Gronthos | ............... | C07K 16/40 435/325 |
| 8,828,375 B2 * | 9/2014 | Itescu | .................. | C12N 5/0647 424/85.1 |
| 8,894,972 B2 * | 11/2014 | Itescu et al. | .................... | 424/9.1 |
| 8,940,293 B2 * | 1/2015 | Li et al. | ........................ | 424/93.7 |
| 9,090,678 B2 * | 7/2015 | Gronthos | ............... | C07K 16/18 |
| 9,415,072 B2 * | 8/2016 | Itescu | .................. | C12N 5/0647 |
| 2009/0029912 A1 * | 1/2009 | Gronthos | ............. | C12N 5/0663 514/1.1 |
| 2009/0053182 A1 * | 2/2009 | Ichim et al. | .................. | 424/93.7 |
| 2009/0074728 A1 * | 3/2009 | Gronthos | ............... | C07K 16/40 424/93.7 |
| 2011/0217263 A1 * | 9/2011 | Itescu | .................. | C12N 5/0647 424/85.2 |
| 2011/0223668 A1 * | 9/2011 | Gronthos | ............. | C12N 5/0663 435/440 |
| 2012/0269774 A1 * | 10/2012 | Ichim | ..................... | A61K 35/28 424/93.7 |
| 2013/0156726 A1 * | 6/2013 | Ichim et al. | .................. | 424/85.1 |
| 2013/0171099 A1 * | 7/2013 | Itescu | .................... | A61K 45/06 424/85.2 |
| 2013/0209417 A1 * | 8/2013 | Gronthos | ............... | C07K 16/40 424/93.7 |
| 2015/0004146 A1 * | 1/2015 | Peled | ..................... | A61K 35/28 424/93.7 |
| 2015/0072422 A1 * | 3/2015 | Gronthos | ............. | C12N 5/0663 435/373 |
| 2015/0267171 A1 * | 9/2015 | Gronthos | ............... | C07K 16/40 424/93.7 |
| 2016/0264683 A1 * | 9/2016 | Gronthos | ............... | C07K 16/40 |
| 2017/0106023 A1 * | 4/2017 | Itescu | .................... | A61K 35/28 |
| 2017/0258846 A1 * | 9/2017 | Itescu | .................... | A61K 45/06 |

FOREIGN PATENT DOCUMENTS

| | | | | |
|---|---|---|---|---|
| JP | 2007-535302 A | 12/2007 | | |
| JP | 2008-543340 A | 12/2008 | | |
| WO | WO 2004084921 A1 * | 10/2004 | ............ | A61K 35/28 |
| WO | WO 2005/046596 A2 | 5/2005 | | |
| WO | WO 2007/002261 A2 | 1/2007 | | |

(Continued)

OTHER PUBLICATIONS

't Hart et al. Curr. Opin. Neurol. 2003. 16: 375-383.*

(Continued)

*Primary Examiner* — Chang-Yu Wang
(74) *Attorney, Agent, or Firm* — John P. White; Cooper & Dunham LLP

(57) ABSTRACT

The present disclosure provides a method for treating an inflammatory neurological disease comprising administering a population of cells enriched for STRO-1+ cells and/or progeny thereof and/or soluble factors derived therefrom.

9 Claims, 8 Drawing Sheets

Specification includes a Sequence Listing.

(56) References Cited

FOREIGN PATENT DOCUMENTS

| WO | WO 2008/036374 A2 | 3/2008 | |
|----|----|----|----|
| WO | WO 2008/052046 A2 | 5/2008 | |
| WO | WO 2008/148105 A1 | 12/2008 | |
| WO | WO 2010/025506 A1 | 3/2010 | |
| WO | WO 2010025506 A1 * | 3/2010 | ............. C12N 5/071 |
| WO | WO 2010/057260 A1 | 5/2010 | |
| WO | WO 2010/090843 A2 | 8/2010 | |
| WO | WO 2012/000065 A1 | 1/2012 | |

OTHER PUBLICATIONS

Bowie et al. Science, 1990, 247:1306-1310.*
Pawson et al. 2003, Science 300:445-452.*
Burgess et al. J of Cell Bio. 1990, 111:2129-2138.*
Francois et al. (2005). Stro-1 Positive and Stro-1 Negative Human Mesenchymal Stem Cells Express Different Levels of immunosuppression. *Blood (ASH Annual Meeting Abstracts)*, 106, Abstract 2305.
Nasef et al. (2007). Selected Stro-1-enriched bone marrow stromal cells display a major suppressive effect on lymphocyte proliferation. *International Journal of Laboratory Hematology*, 31(1), 9-19.
Miller and Bai (2007). Cellular approaches for stimulating CNS remyelination. *Regeneration Medicine*, 2(5), 817-829.
Notification of Transmittal of the International Search Report and the Written Opinion of the International Searching Authority, or the Declaration, including an International Search Report and Written Opinion of the International Searching Authority, dated Jul. 12, 2012 in connection with PCT International Application No. PCT/AU2012/000626, filed Jun. 4, 2012.
Notification Concerning Transmittal of International Preliminary Report on Patentability (Chapter I of the Patent Cooperation Treaty), including an International Preliminary Report on Patentability and Written Opinion of the International Searching Authority, dated Dec. 19, 2013 by The International Bureau of WIPO in connection with PCT International Application No. PCT/AU2012/000626, filed Jun. 4, 2012.
First Office Action, dated Jun. 7, 2016 in connection with corresponding Chinese Patent Application No. 201280033785.1.
Burt, "Finding a less toxic stem cell therapy for multiple sclerosis", Blood, 106(5):1514-1515 (2005).
English translation of "A doctoral dissertation from the Third Military Medical University", Third Military Medical University (2005).
Zhang et al. "Immunosuppressive action of Stro 1+ and Stro 1− subgroups of human mesenchymal stem cells", Med. J. Chin. PLA 32(10):1040-1043 (2007).
Aug. 15, 2014 First Examination Report issued in connection with Australian Patent Application No. 2012262675.
International Preliminary Report on Patentability, dated Aug. 19, 2014, and Corrected Version of Written Opinion of the International Searching Authority, dated Jul. 12, 2012 by The International Bureau of WIPO in connection with PCT International Application No. PCT/AU2012/000626, filed Jun. 4, 2012.
Oct. 14, 2014 Written Opinion, issued in connection with Singaporean Patent Application No. 2013086814.
Oct. 30, 2014 Extended European Search Report, issued in connection with European Patent Application No. 12792873.7.
English Language Translation of Feb. 8, 2016 First Examination Report, issued in connection with Japanese Patent Application No. 2014-513004.
Feb. 12, 2016 First Examination Report, issued in connection with European Patent Application No. 12792873.7.
Oct. 25, 2016 Second Examination Report, issued in connection with European Patent Application No. 12792873.7.
English Language Translation of Nov. 7, 2016 First Office Action, issued in connection with Israeli Patent Application No. 229705.
English Language Translation of Jan. 16, 2017 Second Examination Report, issued in connection with Japanese Patent Application No. 2014-513004.
Mar. 1, 2017 Second Office Action, issued in connection with Chinese Patent Application No. 201280033785.1.
English Language Translation of Apr. 24, 2017 Third Examination Report, issued in connection with Japanese Patent Application No. 2014-513004.
Aug. 3, 2017 Third Office Action, issued in connection with Chinese Patent Application No. 201280033785.1.
English Language Translation of Aug. 23, 2017 Second Office Action, issued in connection with Israeli Patent Application No. 229705.
Ho, A. D. et al. (2008) "Heterogeneity of mesenchymal stromal cell preparations," Cytotherapy 10(4): 320-330.
Itescu, S. et al. (2007) "Mesenchymal Progenitor Cells for Vascular Network Formation and Cardiac Muscle Regeneration," Contemporary Cardiology: Stem Cells and Myocardial Regeneration 57-66.
Rojewski, M. T. et al. (2008) "Phenotypic Characterization of Mesenchymal Stem Cells from Various Tissues," Transfus Med Hemother 35(3): 168-184.
Uccelli, A. and Prockop, D. J. (2010) "Why should mesenchymal stem cells (MSCs) cure autoimmune diseases?" Current Opinion in Immunology 22(6): 768-774.
Zappia, E. et al. (2005) "Mesenchymal stem cells ameliorate experimental autoimmune encephalomyelitis inducing T-cell anergy," Blood 106(5): 1755-1761.

* cited by examiner

SEQUENCE LISTING

```
<160> NUMBER OF SEQ ID NOS: 36

<210> SEQ ID NO 1
<211> LENGTH: 20
<212> TYPE: DNA
<213> ORGANISM: artificial
<220> FEATURE:
<223> OTHER INFORMATION: oligonucleotide for amplifying GAPDH

<400> SEQUENCE: 1
cactgacacg ttggcagtgg                                              20

<210> SEQ ID NO 2
<211> LENGTH: 20
<212> TYPE: DNA
<213> ORGANISM: artificial
<220> FEATURE:
<223> OTHER INFORMATION: oligonucleotide for amplifying GAPDH

<400> SEQUENCE: 2
catggagaag gctggggctc                                              20

<210> SEQ ID NO 3
<211> LENGTH: 20
<212> TYPE: DNA
<213> ORGANISM: artificial
<220> FEATURE:
<223> OTHER INFORMATION: oligonucleotide for amplifying SDF-1

<400> SEQUENCE: 3
gagacccgcg ctcgtccgcc                                              20

<210> SEQ ID NO 4
<211> LENGTH: 21
<212> TYPE: DNA
<213> ORGANISM: artificial
<220> FEATURE:
<223> OTHER INFORMATION: oligonucleotide for amplifying SDF-1

<400> SEQUENCE: 4
gctggactcc tactgtaagg g                                            21
```

```
<210> SEQ ID NO 5
<211> LENGTH: 22
<212> TYPE: DNA
<213> ORGANISM: artificial
<220> FEATURE:
<223> OTHER INFORMATION: oligonucleotide for amplifying IL-1beta

<400> SEQUENCE: 5
aggaagatgc tggttccctc tc                                              22

<210> SEQ ID NO 6
<211> LENGTH: 23
<212> TYPE: DNA
<213> ORGANISM: artificial
<220> FEATURE:
<223> OTHER INFORMATION: oligonucleotide for amplifying IL-1beta

<400> SEQUENCE: 6
cagttcagtg atcgtacagg tgc                                             23

<210> SEQ ID NO 7
<211> LENGTH: 29
<212> TYPE: DNA
<213> ORGANISM: artificial
<220> FEATURE:
<223> OTHER INFORMATION: oligonucleotide for amplifying FLT-1

<400> SEQUENCE: 7
tcactatgga agatctgatt tcttacagt                                       29

<210> SEQ ID NO 8
<211> LENGTH: 25
<212> TYPE: DNA
<213> ORGANISM: artificial
<220> FEATURE:
<223> OTHER INFORMATION: oligonucleotide for amplifying FLT-1

<400> SEQUENCE: 8
ggtataaata cacatgtgct tctag                                           25

<210> SEQ ID NO 9
<211> LENGTH: 20
<212> TYPE: DNA
<213> ORGANISM: artificial
<220> FEATURE:
<223> OTHER INFORMATION: oligonucleotide for amplifying TNFalpha

<400> SEQUENCE: 9
tcagatcatc ttctcgaacc                                                 20

<210> SEQ ID NO 10
<211> LENGTH: 20
<212> TYPE: DNA
<213> ORGANISM: artificial
<220> FEATURE:
<223> OTHER INFORMATION: oligonucleotide for amplifying TNFalpha

<400> SEQUENCE: 10
cagatagatg ggctcatacc                                                 20

<210> SEQ ID NO 11
<211> LENGTH: 20
<212> TYPE: DNA
<213> ORGANISM: artificial
<220> FEATURE:
<223> OTHER INFORMATION: oligonucleotide for amplifying KDR
```

<400> SEQUENCE: 11
tatagatggt gtaacccgga                                              20

<210> SEQ ID NO 12
<211> LENGTH: 21
<212> TYPE: DNA
<213> ORGANISM: artificial
<220> FEATURE:
<223> OTHER INFORMATION: oligonucleotide for amplifying KDR

<400> SEQUENCE: 12
tttgtcactg agacagcttg g                                            21

<210> SEQ ID NO 13
<211> LENGTH: 21
<212> TYPE: DNA
<213> ORGANISM: artificial
<220> FEATURE:
<223> OTHER INFORMATION: oligonucleotide for amplifying RANK-ligand

<400> SEQUENCE: 13
aacaggcctt tcaaggagct g                                            21

<210> SEQ ID NO 14
<211> LENGTH: 22
<212> TYPE: DNA
<213> ORGANISM: artificial
<220> FEATURE:
<223> OTHER INFORMATION: oligonucleotide for amplifying RANK-ligand

<400> SEQUENCE: 14
taaggagggg ttggagacct cg                                           22

<210> SEQ ID NO 15
<211> LENGTH: 20
<212> TYPE: DNA
<213> ORGANISM: artificial
<220> FEATURE:
<223> OTHER INFORMATION: oligonucleotide for amplifying Leptin

<400> SEQUENCE: 15
atgcattggg aaccctgtgc                                              20

<210> SEQ ID NO 16
<211> LENGTH: 20
<212> TYPE: DNA
<213> ORGANISM: artificial
<220> FEATURE:
<223> OTHER INFORMATION: oligonucleotide for amplifying Leptin

<400> SEQUENCE: 16
gcacccaggg ctgaggtcca                                              20

<210> SEQ ID NO 17
<211> LENGTH: 21
<212> TYPE: DNA
<213> ORGANISM: artificial
<220> FEATURE:
<223> OTHER INFORMATION: oligonucleotide for amplifying CBFA-1

<400> SEQUENCE: 17
gtggacgagg caagagtttc a                                            21

```
<210> SEQ ID NO 18
<211> LENGTH: 21
<212> TYPE: DNA
<213> ORGANISM: artificial
<220> FEATURE:
<223> OTHER INFORMATION: oligonucleotide for amplifying CBFA-1

<400> SEQUENCE: 18
tggcaggtag gtgtggtagt g                                            21

<210> SEQ ID NO 19
<211> LENGTH: 28
<212> TYPE: DNA
<213> ORGANISM: artificial
<220> FEATURE:
<223> OTHER INFORMATION: oligonucleotide for amplifying PPARgamma2

<400> SEQUENCE: 19
aactgcgggg aaacttggga gattctcc                                     28

<210> SEQ ID NO 20
<211> LENGTH: 26
<212> TYPE: DNA
<213> ORGANISM: artificial
<220> FEATURE:
<223> OTHER INFORMATION: oligonucleotide for amplifying PPARgamma2

<400> SEQUENCE: 20
aataataagg tggagatgca ggctcc                                       26

<210> SEQ ID NO 21
<211> LENGTH: 21
<212> TYPE: DNA
<213> ORGANISM: artificial
<220> FEATURE:
<223> OTHER INFORMATION: oligonucleotide for amplifying OCN

<400> SEQUENCE: 21
atgagagccc tcacactcct c                                            21

<210> SEQ ID NO 22
<211> LENGTH: 19
<212> TYPE: DNA
<213> ORGANISM: artificial
<220> FEATURE:
<223> OTHER INFORMATION: oligonucleotide for amplifying OCN

<400> SEQUENCE: 22
cgtagaagcg ccgataggc                                               19

<210> SEQ ID NO 23
<211> LENGTH: 20
<212> TYPE: DNA
<213> ORGANISM: artificial
<220> FEATURE:
<223> OTHER INFORMATION: oligonucleotide for amplifying MyoD

<400> SEQUENCE: 23
aagcgccatc tcttgaggta                                              20

<210> SEQ ID NO 24
<211> LENGTH: 20
<212> TYPE: DNA
<213> ORGANISM: artificial
<220> FEATURE:
<223> OTHER INFORMATION: oligonucleotide for amplifying MyoD
```

```
<400> SEQUENCE: 24
gcgagaaacg tgaacctagc                                          20

<210> SEQ ID NO 25
<211> LENGTH: 20
<212> TYPE: DNA
<213> ORGANISM: artificial
<220> FEATURE:
<223> OTHER INFORMATION: oligonucleotide for amplifying SMMHC

<400> SEQUENCE: 25
ctgggcaacg tagtaaaacc                                          20

<210> SEQ ID NO 26
<211> LENGTH: 20
<212> TYPE: DNA
<213> ORGANISM: artificial
<220> FEATURE:
<223> OTHER INFORMATION: oligonucleotide for amplifying SMMHC

<400> SEQUENCE: 26
tatagctcat tgcagcctcg                                          20

<210> SEQ ID NO 27
<211> LENGTH: 21
<212> TYPE: DNA
<213> ORGANISM: artificial
<220> FEATURE:
<223> OTHER INFORMATION: oligonucleotide for amplifying GFAP

<400> SEQUENCE: 27
ctgttgccag agatggaggt t                                        21

<210> SEQ ID NO 28
<211> LENGTH: 20
<212> TYPE: DNA
<213> ORGANISM: artificial
<220> FEATURE:
<223> OTHER INFORMATION: oligonucleotide for amplifying GFAP

<400> SEQUENCE: 28
tcatcgctca ggaggtcctt                                          20

<210> SEQ ID NO 29
<211> LENGTH: 24
<212> TYPE: DNA
<213> ORGANISM: artificial
<220> FEATURE:
<223> OTHER INFORMATION: oligonucleotide for amplifying nestin

<400> SEQUENCE: 29
ggcagcgttg gaacagaggt tgga                                     24

<210> SEQ ID NO 30
<211> LENGTH: 24
<212> TYPE: DNA
<213> ORGANISM: artificial
<220> FEATURE:
<223> OTHER INFORMATION: oligonucleotide for amplifying nestin

<400> SEQUENCE: 30
ctctaaactg gagtggtcag ggct                                     24
```

```
<210> SEQ ID NO 31
<211> LENGTH: 21
<212> TYPE: DNA
<213> ORGANISM: artificial
<220> FEATURE:
<223> OTHER INFORMATION: oligonucleotide for amplifying SOX9

<400> SEQUENCE: 31
ctctgcctgt ttggactttg t                                              21

<210> SEQ ID NO 32
<211> LENGTH: 21
<212> TYPE: DNA
<213> ORGANISM: artificial
<220> FEATURE:
<223> OTHER INFORMATION: oligonucleotide for amplifying SOX9

<400> SEQUENCE: 32
cctttgcttg cctttacct c                                               21

<210> SEQ ID NO 33
<211> LENGTH: 20
<212> TYPE: DNA
<213> ORGANISM: artificial
<220> FEATURE:
<223> OTHER INFORMATION: oligonucleotide for amplifying collagen type X

<400> SEQUENCE: 33
agccagggtt gccaggacca                                                20

<210> SEQ ID NO 34
<211> LENGTH: 20
<212> TYPE: DNA
<213> ORGANISM: artificial
<220> FEATURE:
<223> OTHER INFORMATION: oligonucleotide for amplifying collagen type X

<400> SEQUENCE: 34
ttttcccact ccaggagggc                                                20

<210> SEQ ID NO 35
<211> LENGTH: 20
<212> TYPE: DNA
<213> ORGANISM: artificial
<220> FEATURE:
<223> OTHER INFORMATION: oligonucleotide for amplifying aggrecan

<400> SEQUENCE: 35
cactgttacc gccacttccc                                                20

<210> SEQ ID NO 36
<211> LENGTH: 20
<212> TYPE: DNA
<213> ORGANISM: artificial
<220> FEATURE:
<223> OTHER INFORMATION: oligonucleotide for amplifying aggrecan

<400> SEQUENCE: 36
accagcggaa gtccccttcg                                                20
```

METHODS OF TREATING MULTIPLE SCLEROSIS USING STRO-1+ AND TNAP+ MULTIPOTENTIAL CELLS

CROSS-REFERENCE TO RELATED APPLICATIONS

This application is a § 371 national stage of PCT International Application No. PCT/AU2012/000626, filed Jun. 4, 2012, claiming the benefit of U.S. Provisional Application No. 61/493,073, filed Jun. 3, 2011, the contents of each of which are hereby incorporated by reference in their entirety.

REFERENCE TO SEQUENCE LISTING

This application incorporates-by-reference nucleotide and/or amino acid sequences which are present in the file named "131203_2251_82982_A_PCT_US_Substitute_Sequence_Listing_BI.txt," which is 7.37 kilobytes in size, and which was created Dec. 2, 2013 in the IBM-PC machine format, having an operating system compatibility with MS-Windows, which is contained in the text file filed Dec. 3, 2013 as part of this application.

FIELD

The present disclosure relates to methods for treating or preventing neurological diseases.

BACKGROUND

Inflammatory neurological diseases are a class of conditions in which a subject's immune system targets or attacks components of the neurological system. These diseases can result from the immune system attacking, for example, neurons, Schwann cells or other cells of the nervous system myelin or neurotransmitters. In some cases, the inflammatory neurological disease may be a complication or a component of an existing disease, e.g., Exemplary inflammatory neurological diseases include multiple sclerosis, systemic lupus erythematosus (SLE), Guillain-Barre syndrome, Lambert-Eaton myasthenic syndrome, myasthenia gravis, transverse myelitis, leukodystrophy or progressive multifocal leukoencephalopathy.

MS is one of the more common inflammatory neurological diseases. It is an inflammatory and demyelinating degenerative disease of the human central nervous system (CNS). It is a worldwide disease that affects approximately 300,000 people in the United States alone. The majority of people affected by MS (about 70%-80% of cases) show onset between 20 and 40 years of age. MS is a heterogeneous disorder based on clinical course, magnetic resonance imaging (MRI) scan assessment, and pathology analysis of biopsy and autopsy material. The disease manifests itself in a large number of possible combinations of deficits, including spinal cord, brainstem, cranial nerve, cerebellar, cerebral, and cognitive syndromes. Progressive disability is the fate of most patients with MS. About half of MS patients require a cane to walk within 15 years of disease onset.

MS presents in most cases (about 80%) with clinical relapses characterized by fully or partially-reversible focal neurological deficits. This form of MS is known as relapsing-remitting MS (RRMS), and is dominated by inflammation and oedema. Active inflammation of the CNS is visualized as gadolinium enhancing white matter lesions on MRI. After a median of about 39 years, about half of RRMS cases gradually accumulate irreversible neurologic deficits in the absence of clinical relapses or new white matter lesions as detected by MRI. This stage of disease is known as secondary progressive MS (SPMS) or chronic disease. The 20% of patients who do not present with RRMS present with progressive clinical deterioration from the onset of disease, which is known as primary progressive MS (PPMS), which is another form of chronic disease.

Currently, acute MS relapses are usually treated with high-dose, short-term intravenous corticosteroids. This treatment shortens relapse duration but does not improve the degree of recovery or the long-term course of disease. There are currently several approved disease-modifying therapies approved in USA, which are intended to lower the clinical relapse rate, extend the time to next relapse and/or reduce the accumulation of new lesions on MRI. However, these therapies are only moderately effective for treating MS, particularly during the relapsing-remitting phase. These treatments also merely retard the progression of disease and do not result in remyelination.

SLE is an inflammatory disease affecting various organ systems in the body. Subjects suffering from SLE can develop various neurological disorders such as headaches, personality changes, organic brain syndrome, peripheral neuropathies, sensory neuropathy, psychological problems including paranoia, mania, and schizophrenia, seizures, transverse myelitis, and paralysis and stroke. Some of these changes can be brought on by antiphospholipid antibodies (e.g., anti-cardiolipin antibodies), which can bind to cells of the central nervous system and disrupt function and/or thrombosis.

Common pharmacological treatments for lupus include the use of corticosteroids or immunosuppressive drugs, both of which have undesirable side effects and merely treat the symptoms as they occur.

Other inflammatory neurological diseases are treated using, for example, immunosuppressive drugs, corticosteroids, plasmapheresis or intravenous immunoglobulin, each of which carry a risk of infection or other adverse side effect.

It will therefore be apparent to those skilled in the art that there is a need in the art for new therapies useful for treating inflammatory neurological diseases.

SUMMARY

The inventors have studied the effect of STRO-1+ multipotential cell preparations in an accepted animal models of an inflammatory neurological disease, i.e., chronic paralytic experimental inflammatory encephalomyelitis (EAE). The inventors found that STRO-1+ cells administered after induction of EAE reduced the severity of the disease.

The inventors also found that STRO-1+ cells prevented an immune response against an antigen by T cells derived from an animal previously immunized with the antigen.

The present disclosure provides a method for treating or preventing an inflammatory neurological disease, the method comprising administering to the subject a population of cells enriched for STRO-1+ cells and/or progeny thereof and/or soluble factors derived therefrom.

In one example, the inflammatory neurological disease is associated with or caused by a T cell response to an inflammatory stimulus.

In one example, the method comprises administering a population of cells enriched for STRO-1$^{bright}$ cells and/or progeny thereof and/or soluble factors derived therefrom.

In one example, the inflammatory neurological disease is selected from the group consisting of multiple sclerosis, systemic lupus erythematosus, Guillain-Barre syndrome, Lambert-Eaton myasthenic syndrome, myasthenia gravis, transverse myelitis, leukodystrophy and progressive multifocal leukoencephalopathy.

In one example, the disease is systemic lupus erythematosus.

In another example, the disease is multiple sclerosis. In one example, the disease is a chronic progressive form of multiple sclerosis. In another example, the disease is a relapsing-remitting form of multiple sclerosis.

In one example, the method comprises administering a population of cells enriched for STRO-1$^{bright}$ cells and/or progeny thereof and/or soluble factors derived therefrom. In one example, the progeny are additionally enriched for STRO-1$^{bright}$ cells.

Exemplary cells and/or progeny additionally express tissue non-specific alkaline phosphatase (TNAP) and/or heat shock protein 90β (HSP90p) and/or CD 146.

In one example, the population of cells is derived from bone marrow or dental pulp.

In one example, the population enriched for STRO-1$^+$ cells and/or progeny thereof and/or soluble factors derived therefrom are administered systemically. For example, the population of cells enriched for Stro-1$^+$ cells and/or progeny cells thereof and/or soluble factors derived therefrom may be administered intravenously, intra-arterially, intramuscularly, subcutaneously, into an aorta, into an atrium or ventricle of the heart or into a blood vessel connected to an organ affected by the inflammatory neurological disease. For example, the population and/or progeny and/or soluble factors are administered intravenously.

In another example, the population enriched for STRO-1$^+$ cells and/or progeny thereof and/or soluble factors derived therefrom are administered into cerebral spinal fluid or into the central nervous system.

In a further example, the population enriched for STRO-1$^+$ cells and/or progeny thereof and/or soluble factors derived therefrom are administered to a site of disease, e.g., to a site of myelin degeneration.

In the case of a relapsing-remitting disease (e.g., relapsing-remitting MS), the cells can be administered during disease relapse to prevent or delay relapse of the disease.

In one example, the method comprises administering an effective amount of the population enriched for STRO-1$^+$ cells and/or progeny thereof and/or soluble factors derived therefrom. In one example, the effective amount is an amount sufficient to increase the number of regulatory T (Treg) cells in the subject and/or at the site of pathogenesis.

An exemplary method described herein according to any example, comprises administering a dose of the population and/or the progeny and/or the soluble factors sufficient to improve a clinical measure of the inflammatory neurological disease and/or to reduce or prevent an immune response against an antigen associated with the inflammatory neurological disease.

In one example, the method comprises administering an effective dose or a therapeutically effective dose of the population and/or progeny and/or soluble factors.

In one example, the method comprises administering between $1\times10^4$ to $5\times10^6$ STRO-1$^+$ cells and/or progeny thereof per kg. For example, the method comprises administering between $1\times10^5$ to $1\times10^6$ STRO-1$^+$ cells and/or progeny thereof per kg. For example, the method comprises administering between $2\times10^5$ to $8\times10^5$ STRO-1$^+$ cells and/or progeny thereof per kg. For example, the method comprises administering about $2\times10^5$ STRO-1$^+$ cells and/or progeny thereof per kg or about $4\times10^5$ STRO-f cells and/or progeny thereof per kg or about $8\times10^5$ STRO-1$^+$ cells and/or progeny thereof per kg.

In one example, a method described herein according to any example, comprises administering a low dose of STRO-1$^+$ cells and/or progeny thereof. For example, the low dose of STRO-1$^+$ cells and/or progeny thereof comprises between $1\times10^3$ and $3\times10^5$ STRO-1$^+$ cells and/or progeny thereof per kg.

In one example, the population and/or the progeny and/or the soluble factors are administered a plurality of times. For example, the population and/or the progeny and/or the soluble factors are administered a plurality of times in one week or once every four or more weeks.

In one example, the population and/or the progeny and/or the soluble factors are administered during a remission of an inflammatory neurological condition.

In another example, the population enriched for STRO-1$^+$ cells and/or progeny thereof are genetically-engineered to express a molecule to block stimulation of T cells and/or the soluble factors are from such genetically-modified cells.

In another example, the population enriched for STRO-1$^+$ cells and/or progeny thereof and/or soluble factors therefrom are administered with a compound to block stimulation of T cells.

The population enriched for STRO-1$^+$ cells and/or progeny cells can be autogeneic or allogeneic and/or the soluble factors can be derived from autogeneic or allogeneic cells. In one example, the population of cells and/or progeny cells are allogeneic and/or the soluble factors are derived from autogeneic cells.

In one example, the population enriched for STRO-1$^+$ cells and/or progeny cells have been culture expanded prior to administration and/or prior to obtaining the soluble factors.

In another example, a method described herein further comprises administering an immunosuppressive agent. The immunosuppressive agent may be administered for a time sufficient to permit said transplanted cells to be functional.

The present disclosure also provides a method for preventing an immune response in response to an antigen, the method comprising administering to the subject a population of cells enriched for STRO-1$^+$ cells and/or progeny thereof and/or soluble factors derived therefrom.

In one example, the immune response is a T cell-mediated immune response. An exemplary T cell-mediated immune response comprises T cell proliferation.

In one example, the T cell-mediated immune response is suppressed in response to a specific antigen and a T cell-mediated immune response in response to another antigen is not suppressed.

In one example, the subject has previously raised an immune response to the antigen and the population, progeny and/or soluble factors suppress a further immune response to the antigen.

In one example, the population, progeny and/or soluble factors are administered after the subject raises an immune response to the antigen to thereby prevent a further immune response to the antigen.

In one example, the immune response is suppressed for at least about 24 days following administration of the population of cells enriched for STRO-1$^+$ cells and/or progeny thereof and/or soluble factors derived therefrom.

The present disclosure also provides a method for inducing tolerance to an antigen in a subject, the method comprising administering to the subject a population of cells enriched for STRO-1+ cells and/or progeny thereof and/or soluble factors derived therefrom.

In one example of a method described herein the antigen or the specific antigen is one against which an inflammatory response is raised. For example, the inflammatory response is causative of an inflammatory neurological disease.

In one example of a method described herein according to any example, the population of cells enriched for STRO-1+ cells and/or progeny thereof and/or soluble factors derived therefrom is administered with a compound that treats or prevents an inflammatory neurological disease. An exemplary compound is glatiramer acetate and/or beta interferon.

The compound can be mixed with the population and/or progeny and/or soluble factors or administered at the same time and/or administered before or after the population and/or progeny and/or soluble factors (e.g., such that the compound and the population and/or progeny and/or soluble factors are providing a benefit at the same time).

The present disclosure also provides a population of cells enriched for STRO-1+ cells and/or progeny thereof and/or soluble factors derived therefrom for use in the treatment or prevention of an inflammatory neurological disease and/or for suppressing a T cell-mediated immune response against an antigen and/or for inducing tolerance to an antigen.

The present disclosure also provides for use of a population of cells enriched for STRO-1+ cells and/or progeny thereof and/or soluble factors derived therefrom in the manufacture of a medicament for treating or preventing an inflammatory neurological disease and/or for suppressing a T cell-mediated immune response against an antigen and/or for inducing tolerance to an antigen.

Each example of the disclosure shall be taken to apply to a method for reducing, delaying or preventing myelin destruction and/or an inflammatory response against myelin or a component thereof.

Each example of the disclosure shall be taken to apply to inflammation in the nervous system or a component thereof, Each example of the disclosure shall be taken to apply to a method for inducing or promoting remyelination or neurite outgrowth.

KEY TO SEQUENCE LISTING

Figure 1:
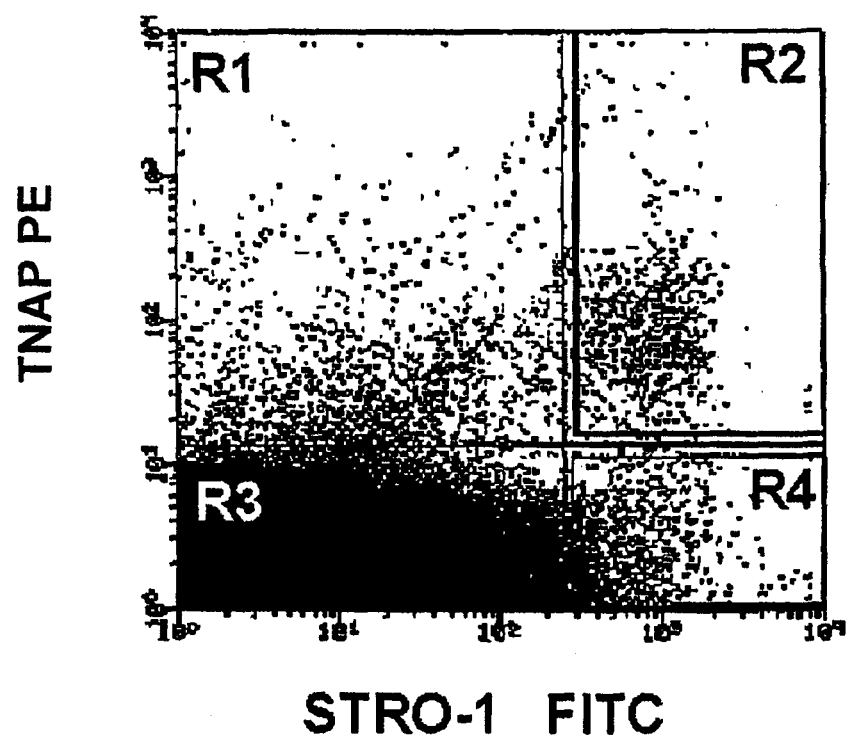
FIG. 1. Co-expression of TNAP (STRO-3) and the Mesenchymal Precursor Cell Marker, STRO-1$^{bright}$ by Adult Human bone marrow morphonuclear cells (BMMNC). Dual-color immunofluorescence and flow cytometry was performed by incubation of STRO-1 MACS-selected BMMNC and indirectly labeled with a goat anti-murine IgM antibody coupled to FITC (x axis), and STRO-3 mAb (murine IgG1) indirectly labeled with a goat anti-murine IgG coupled to PE (y axis). The dot plot histogram represents 5×104 events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1+ cells failed to react with the STRO-3 mAb.

SEQ ID NO: 1 oligonucleotide for amplifying nucleic acid encoding GAPDH
SEQ ID NO: 2 oligonucleotide for amplifying nucleic acid encoding GAPDH
SEQ ID NO: 3 oligonucleotide for amplifying nucleic acid encoding SDF-1
SEQ ID NO: 4 oligonucleotide for amplifying nucleic acid encoding SDF-1
SEQ ID NO: 5 oligonucleotide for amplifying nucleic acid encoding IL-1β

SEQ ID NO: 6 oligonucleotide for amplifying nucleic acid encoding IL-1β
SEQ ID NO: 7 oligonucleotide for amplifying nucleic acid encoding FLT-1
SEQ ID NO: 8 oligonucleotide for amplifying nucleic acid encoding FLT-1
SEQ ID NO: 9 oligonucleotide for amplifying nucleic acid encoding TNF-a
SEQ ID NO: 10 oligonucleotide for amplifying nucleic acid encoding TNF-a
SEQ ID NO: 11 oligonucleotide for amplifying nucleic acid encoding KDR
SEQ ID NO: 12 oligonucleotide for amplifying nucleic acid encoding KDR
SEQ ID NO: 13 oligonucleotide for amplifying nucleic acid encoding RANKL
SEQ ID NO: 14 oligonucleotide for amplifying nucleic acid encoding RANKL
SEQ ID NO: 15 oligonucleotide for amplifying nucleic acid encoding Leptin
SEQ ID NO: 16 oligonucleotide for amplifying nucleic acid encoding Leptin
SEQ ID NO: 17 oligonucleotide for amplifying nucleic acid encoding CBFA-1
SEQ ID NO: 18 oligonucleotide for amplifying nucleic acid encoding CBFA-1
SEQ ID NO: 19 oligonucleotide for amplifying nucleic acid encoding PPARy2
SEQ ID NO: 20 oligonucleotide for amplifying nucleic acid encoding PPARy2
SEQ ID NO: 21 oligonucleotide for amplifying nucleic acid encoding OCN
SEQ ID NO: 22 oligonucleotide for amplifying nucleic acid encoding OCN
SEQ ID NO: 23 oligonucleotide for amplifying nucleic acid encoding MyoD
SEQ ID NO: 24 oligonucleotide for amplifying nucleic acid encoding MyoD
SEQ ID NO: 25 oligonucleotide for amplifying nucleic acid encoding SMMHC
SEQ ID NO: 26 oligonucleotide for amplifying nucleic acid encoding SMMHC
SEQ ID NO: 27 oligonucleotide for amplifying nucleic acid encoding GFAP
SEQ ID NO: 28 oligonucleotide for amplifying nucleic acid encoding GFAP
SEQ ID NO: 29 oligonucleotide for amplifying nucleic acid encoding Nestin
SEQ ID NO: 30 oligonucleotide for amplifying nucleic acid encoding Nestin
SEQ ID NO: 31 oligonucleotide for amplifying nucleic acid encoding SOX9
SEQ ID NO: 32 oligonucleotide for amplifying nucleic acid encoding SOX9
SEQ ID NO: 33 oligonucleotide for amplifying nucleic acid encoding Collagen type X
SEQ ID NO: 34 oligonucleotide for amplifying nucleic acid encoding Collagen type X
SEQ ID NO: 35 oligonucleotide for amplifying nucleic acid encoding Aggrecan
SEQ ID NO: 36 oligonucleotide for amplifying nucleic acid encoding Aggrecan

DETAILED DESCRIPTION

General Techniques and Selected Definitions

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied to each and every other example of the disclosure unless specifically stated otherwise.

Those skilled in the art will appreciate that the disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-1 15; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). *Biochem. Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross, E. and Meienhofer, J. eds.), vol. 2, pp. 1-284, Academic Press, New York. 12. Wunsch, E., ed. (1974) Synthese von Peptiden in Houben-Weyls Metoden der Organischen Chemie (Miiler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) *Int. J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified integer may be obtained from a particular source albeit not necessarily directly from that source. In the context of soluble factors derived from STRO-1$^+$ cells and/or progeny cells thereof, this term shall be taken to mean one or more factors, e.g., proteins, peptides, carbohydrates, etc, produced during in vitro culturing of STRO-1$^+$ cells and/or progeny cells thereof.

As used herein, the term "inflammatory neurological disease" shall be taken to include any disorder characterized by a defect in neuronal signaling and/or neuronal dysfunction and/or neuronal cell death resulting from an inflammatory response, and, in some examples, an autoimmune response. In one example, an inflammatory neurological disorder is a disorder associated with or caused by myelin degeneration and/or autoantibodies against a component of the nervous system, such as, for example a component of myelin or a phospholipid or a ganglioside. An inflammatory neurological disease may be a primary disease or may be a complication of an existing disease, e.g., in some cases of SLE.

As used herein, the term "effective amount" shall be taken to mean a sufficient quantity of STRO-1$^+$ cells and/or progeny cells thereof and/or soluble factors derived therefrom to reduce an inflammatory response in a subject that causes or is associated with a neurological disease. For example, an effective amount of STRO-1$^+$ cells and/or progeny cells thereof and/or soluble factors derived therefrom may reduce lesions in the brain or spinal cord, e.g., as detectable using magnetic resonance imaging (MRI) and/or autoantibodies against myelin and/or oligoclonal bands in CSF.

As used herein, the term "therapeutically effective amount" shall be taken to mean a sufficient quantity of STRO-1$^+$ cells and/or progeny cells thereof and/or soluble factors derived therefrom to reduce or inhibit one or more symptoms of a clinical inflammatory neurological disease.

As used herein, the term "prophylactically effective amount" shall be taken to mean a sufficient quantity of STRO-1$^+$ cells and/or progeny cells thereof and/or soluble factors derived therefrom to prevent or inhibit or delay the onset of one or more detectable symptoms of a clinical inflammatory neurological disease.

As used herein, the term "low dose" shall be understood to mean an amount of STRO-1$^+$ cells and/or progeny thereof less than $0.7 \times 10^6$, yet still sufficient to lipid and/or lipoprotein levels in a subject that cause(s) or is(are) associated with an inflammatory neurological disease and/or to treat or prevent a an inflammatory neurological disease. For example, a low dose comprises $0.5 \times 10^6$ or fewer cells, or $0.4 \times 10^6$ or fewer cells or $0.3 \times 10^6$ or fewer cells or $0.2 \times 10^6$ or fewer cells.

As used herein, the term "treat" or "treatment" or "treating" shall be understood to mean administering a therapeutically effective amount of soluble factors and/or cells and reducing or inhibiting at least one symptom of a clinical condition associated with or caused by an inflammatory neurological condition.

As used herein, the term "prevent" or "preventing" or "prevention" shall be taken to mean administering a prophylactically effective amount of soluble factors and/or cells and stopping or hindering or delaying the development or progression of at least one symptom of a clinical inflammatory neurological condition.

As used herein, the term "soluble factors" shall be taken to mean any molecule, e.g., protein, peptide, glycoprotein, glycopeptide, lipoprotein, lipopeptide, carbohydrate, etc. produced by STRO-1$^+$ cells and/or progeny thereof that are water soluble. Such soluble factors may be intracellular and/or secreted by a cell. Such soluble factors may be a complex mixture (e.g., supernatant) and/or a fraction thereof and/or may be a purified factor. In one example of the present disclosure soluble factors are or are contained within supernatant. Accordingly, any example herein directed to administration of one or more soluble factors shall be taken to apply to the administration of supernatant.

As used herein, the term "supernatant" refers to the non-cellular material produced following the in vitro culturing of mesenchymal precursor cells, and/or progeny cells thereof, in a suitable medium, such as liquid medium. Typically, the supernatant is produced by culturing the cells in the medium under suitable conditions and time, followed by removing the cellular material by a process such as centrirugation. The supernatant may or may not have been subjected to further purification steps before administration. In one example, the supernatant comprises less than $10^5$, such as less than $10^4$, for example, less than $10^3$ and such as no live cells.

As used herein, the term "prevents an immune response to an antigen" will be understood to mean that a population and/or progeny and/or soluble factors described herein according to any example delays and/or reduces and/or stops development of an immune response, as opposed to suppressing a pre-existing an immune response. In some examples herein, an example of the disclosure directed to preventing an immune response to an antigen shall be taken to apply to reducing or inhibiting an existing immune response to an antigen.

As used herein, the term "normal or healthy individual" shall be taken to mean a subject that does not suffer from an inflammatory neurological condition as assessed by any method known in the art and/or described herein.

As used herein, the term "glatiramer acetate" will be understood to mean an immunomodulator drug comprising a random polymer of four amino acids found in myelin basic protein, namely glutamic acid, lysine, alanine, and tyrosine currently sold under the trade name Copaxone.

STRO-1$^+$ Cells or Progeny Cells, and Supernatant or One or More Soluble Factors Derived Therefrom STRO-1$^+$ cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm.

In one example, the STRO-1$^+$ cells are multipotential cells which are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. STRO-1$^+$ multipotential cells are thus, non-hematopoietic progenitor cells which divide to yield daughter cells that are either stem cells or are precursor cells which in time will irreversibly differentiate to yield a phenotypic cell.

In one example, the STRO-1$^+$ cells are enriched from a sample obtained from a subject, e.g., a subject to be treated or a related subject or an unrelated subject (whether of the same species or different). The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1$^+$ cells comprises at least about 0.1% or 0.5% or 1% or 2% or 5% or 10% or 15% or 20% or 25% or 30% or 50% or 75% STRO-1$^+$ cells. In this regard, the term "population of cells enriched for STRO-1$^+$ cells" will be taken to provide explicit support for the term "population of cells comprising X % STRO-1$^+$ cells", wherein X % is a percentage as recited herein. The STRO-1$^+$ cells can, in some examples, form clonogenic colonies, e.g. CFU-F (fibroblasts) or a subset thereof (e.g., 50% or 60% or 70% or 70% or 90% or 95%) can have this activity.

In one example, the population of cells is enriched from a cell preparation comprising STRO-1$^+$ cells in a selectable form. In this regard, the term "selectable form" will be understood to mean that the cells express a marker (e.g., a cell surface marker) permitting selection of the STRO-1$^+$ cells. The marker can be STRO-1, but need not be. For example, as described and/or exemplified herein, cells (e.g., MPCs) expressing STRO- and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1$^+$ does not mean that the cells are selected by STRO-1 expression. In one example, the cells are selected based on at least STRO-3 expression, e.g., they are STRO-3$^+$ (TNAP$^+$).

Reference to selection of a cell or population thereof does not require selection from a specific tissue source. As described herein STRO-1$^+$ cells can be selected from or isolated from or enriched from a large variety of sources. That said, in some examples, these terms provide support for selection from any tissue comprising STRO-1$^+$ cells (e.g., MPCs) or vascularized tissue or tissue comprising pericytes (e.g., STRO-1$^+$ pericytes) or any one or more of the tissues recited herein.

In one example, the cells used in the present disclosure express one or more markers individually or collectively selected from the group consisting of TNAP$^+$, VCAM-1$^+$, THY-1$^+$, STRO-4$^+$ (HSP-90β), STRO-2$^+$, CD45$^+$, CD146$^+$, 3G5$^+$ or any combination thereof.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

In one example, the STRO-1$^+$ cells are STRO-1$^{bright}$ (syn. STRO-1$^{bri}$). In one example, the Stro-1$^{bri}$ cells are preferentially enriched relative to STRO-1$^{dim}$ or STRO-1$^{intermediate}$ cells.

In one example, the STRO-1$^{bright}$ cells are additionally one or more of TNAP$^+$, VCAM-1$^+$, THY-1$^{+'}$ STRO-4$^+$ (HSP-90p), STRO-2$^+$ and/or CD146$^+$. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the mesenchymal precursor cells are perivascular mesenchymal precursor cells as defined in WO 2004/85630. For example, the mesenchymal precursor cells express a marker of a perivascular cell, e.g., the cells are STRO-1$^+$ or STRO-1$^{bright}$ and/or 3G5$^+$. In one example, the cells are or were previously or are progeny of cells that were isolated from vascularized tissue or organs or parts thereof.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labeled or is undetectable above background levels, e.g., levels detected suing an isotype control antibody.

The term "bright", when used herein, refers to a marker on a cell surface that generates a relatively high signal when detectably labeled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labeled with a FITC-conjugated STRO-1 antibody as determined by fluorescence activated cell sorting (FACS) analysis, than non-bright cells (STRO-1$^{dull/dim}$). In one example, "bright" cells constitute at least about 0.1% of the most brightly labeled bone marrow mononuclear cells contained in the starting sample. In other examples, "bright" cells constitute at least about 0.1%, at least about 0.5%, at least about 1%, at least about 1.5%, or at least about 2%, of the most brightly labeled bone marrow mononuclear cells contained in the starting sample. In an example, STRO-1$^{bright}$ cells have 2 log magnitude higher expression of STRO-1 surface expression relative to "background", namely cells that are STRO-1$^-$. By comparison, STRO-1$^{dim}$ and/or STRO-1$^{intermediate}$ cells have less than log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In an example, the TNAP is BAP. In an example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in an example, the STRO-1$^+$ cells are capable of giving rise to clonogenic CFU-F.

In one example, a significant proportion of the STRO-1$^+$ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another example, the STRO-1$^+$ cells are not capable of giving rise, upon culturing, to hematopoietic cells.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used. In another useful example of the disclosure, cells of a non-human animal (or if the patient is not a human, from another species) are used.

The present disclosure also contemplates use of supernatant or soluble factors obtained or derived from STRO-1$^+$ cells and/or progeny cells thereof (the latter also being referred to as expanded cells) which are produced from in vitro culture. Expanded cells of the disclosure may a have a wide variety of phenotypes depending on the culture conditions (including the number and/or type of stimulatory factors in the culture medium), the number of passages and the like. In certain examples, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an example, progeny cells useful for the methods of the disclosure are obtained by isolating TNAP$^+$ STRO-1$^+$ cells from bone marrow using magnetic beads labeled with the STRO-3 antibody, and then culture expanding the isolated cells (see Gronthos et al. *Blood* 85: 929-940, 1995 for an example of suitable cultunng conditions).

In one example, such expanded cells (progeny) (for example, at least after 5 passages) can be TNAP$^-$, CC9$^+$, HLA class I$^+$, HLA class II", CD14\ CD19$^-$, CD3", CD 11ac', CD31$^-$, CD86$^-$, CD34" and/or CD80'. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9'). In one example, expanded cells still have the capacity to differentiate into different cell types.

In one example, an expended cell population used to obtain supernatant or soluble factors, or cells per se, comprises cells wherein at least 25%, such as at least 50%, of the cells are CC9$^+$.

In another example, an expanded cell population used to obtain supernatant or soluble factors, or cells per se, comprises cells wherein at least 40%, such as at least 45%, of the cells are STRO-1$^+$.

In a further example, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD 18, CD61, integrin beta 6-19, thrombomodulin, CD 10, CD 13, SCF, PDGF-R, EGF-R, IGF1-R, NGF-R, FGF-R, Leptin-R (STRO-2=Leptin-R), RANKL, STRO-1$^{bright}$ and CD 146 or any combination of these markers.

In one example, the progeny cells are Multipotential Expanded STRO-1$^+$ Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MPCs from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-1$^{bright}$, 3G5$^+$, VCAM-1, THY-1, CD146 and STRO-2.

MEMPS can be distinguished from freshly harvested STRO-1$^+$ multipotential cells in that they are positive for the marker STRO-1$^{bri}$ and negative for the marker Alkaline phosphatase (ALP). In contrast, freshly isolated STRO-1$^+$ multipotential cells are positive for both STRO-1$^{bri}$ and ALP. In an example of the present disclosure, at least 15%, 20%, 30%, 40%, 50%, 60%, 70%, 80%, 90% or 95% of the administered cells have the phenotype STRO-1$^{bri}$, ALP'. In one example the MEMPS are positive for one or more of the markers Ki67, CD44 and/or CD49c/CD29, VLA-3, α3β1. In yet a further example the MEMPs do not exhibit TERT activity and/or are negative for the marker CD 18.

The STRO-1$^+$ cell starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing the present disclosure, separation of cells carrying any given cell surface marker can be effected by a number of different methods, however, some methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, such as monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. In some examples, the separation techniques maximize the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

The method for isolating STRO-1$^+$ cells, for example, comprises a first step being a solid phase sorting step utilizing for example magnetic activated cell sorting (MACS) recognizing high level expression of STRO-1. A second sorting step can then follow, should that be desired, to result in a higher level of precursor cell expression as described in patent specification WO 01/14268. This second sorting step might involve the use of two or more markers.

The method obtaining STRO-1$^+$ cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1$^+$ cell population has been obtained, it may be cultured or expanded by any suitable means to obtain MEMPs.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used to obtain the supernatant or soluble factors. In another useful example of the disclosure, cells of a non-human animal (or if the patient is not a human, from another species) are used to obtain supernatant or soluble factors.

The disclosure can be practiced using cells from any non-human animal species, including but not limited to non-human primate cells, ungulate, canine, feline, lagomorph, rodent, avian, and fish cells. Primate cells with which the disclosure may be performed include but are not limited to cells of chimpanzees, baboons, cynomolgus monkeys, and any other New or Old World monkeys. Ungulate cells with which the disclosure may be performed include but are not limited to cells of bovines, porcines, ovines, caprines, equines, buffalo and bison. Rodent cells with which the disclosure may be performed include but are not limited to mouse, rat, guinea pig, hamster and gerbil cells. Examples of lagomorph species with which the disclosure may be performed include domesticated rabbits, jack rabbits, hares, cottontails, snowshoe rabbits, and pikas. Chickens (*Gallus gallus*) are an example of an avian species with which the disclosure may be performed.

Cells useful for the methods of the disclosure may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present disclosure. In one example, the cells are maintained and stored by using cryo-preservation.

Genetically-Modified Cells

In one example, the STRO-1$^+$ cells and/or progeny cells thereof are genetically modified, e.g., to express and/or secrete a protein of interest, e.g., a protein providing a therapeutic and/or prophylactic benefit, e.g., a polypeptide that reduces or prevents T cell activation or that induces proliferation and/or differentiation of neurons and/or myelin production. Exemplary T cell antagonists include, for example, peptides described in Toda et al, *Eur. J. Immunol.*, 30: 403-414, 2000.

In another example, the STRO-1$^+$ cells and/or progeny cells thereof are genetically modified to express a protein that treats an inflammatory neurological condition, e.g., beta-interferon.

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply to the present example of the disclosure.

For example, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present disclosure, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the disclosure will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for the method of the present disclosure in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Life Technologies Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

Alternatively, an expression construct of the disclosure is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et ai, *J Virol.* 5(5:2731-2739 (1992); Johann et al, *J. Virol.* 65:1635-1640 (1992); Sommerfelt et al, *Virol.* 76:58-59 (1990); Wilson et al, *J. Virol.* 65:274-2318 (1989); Miller et al, *J. Virol.* 65:2220-2224 (1991); PCT/US94/05700; Miller and Rosman *BioTechniques* 7:980-990, 1989; Miller, A. D. *Human Gene Therapy* 7:5-14, 1990; Scarpa et al *Virology* 75:849-852, 1991; Burns et al. *Proc. Natl. Acad. Sci USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al. *Molec. Cell. Biol.* 5:3988-3996, 1988; Vincent et al. (1990) Vaccines 90 (Cold Spring Harbor Laboratory. Press); Carter *Current Opinion in Biotechnology* 5:533-539, 1992; Muzyczka. *Current Topics in Microbiol, and Immunol.* 158:97-129, 1992; Kotin, Human Gene Therapy 5:793-801, 1994; Shelling and Smith *Gene Therapy* 7:165-169, 1994; and Zhou et al. *J Exp. Med.* 779:1867-1875, 1994.

Additional viral vectors useful for delivering an expression construct of the disclosure include, for example, those derived from the pox family of viruses, such as vaccinia virus and avian poxvirus or an alphavirus or a conjugate virus vector (e.g. that described in Fisher-Hoch et ai, *Proc. Natl Acad. Sci. USA* 56:317-321, 1989).

Assaying Therapeutic/Prophylactic Potential of Cells and Soluble Factors

Methods for determining the ability of cells or soluble factors to treat or prevent or delay the onset or progression of an inflammatory neurological condition will be apparent to the skilled artisan.

For example, cells or soluble factors (e.g., a mixture of factors or a single factor or a fraction of factors (e.g., derived by affinity purification or chromatography)) are screened to identify therapeutic agents in in vitro models of components of inflammatory neurological disease (e.g., MS) pathology. Exemplary models include those making use of isolated T cells or mixed lymphocyte populations from transgenic mouse models of MS that comprise a transgenic T cell receptor that reacts with a component of the sheath, e.g., myelin basic protein, myelin oligodendrocyte glycoprotein or myelin proteolipid protein. The cells are contacted with the myelin protein in the presence and absence of cells and/or soluble factors and the level of inflammatory response is assessed, e.g., by detecting secretion of pro-inflammatory cytokines, such as interleukin (IL)-2 or interferon γ. Alternatively, or in addition, proliferative response of cells is assessed, e.g., using ($^3$H)thymidine incorporation. Cells and/or soluble factors that reduce an inflammatory response are selected as a therapeutic. Exemplary assays are described in Illes et ai, *Proc. Natl. Acad. Sci. USA,* 101:1 1749-1 1754, 2004 or Rossi et ai, *J. Biomolecular Screening,* 12: 481-489, 2007.

Cells and/or soluble factors are also tested in in vivo models of inflammatory neurological disease. Exemplary models include EAE models in which a mouse or rat is immunized with a myelin sheath protein or peptide derived therefrom (e.g., MOG, MBP or PLP) and an immune response is generated against the protein thereby inducing a model of MS. Alternatively, T cells that are immunoreactive with a myelin sheath protein are introduced into mice or rats to induce EAE. Exemplary EAE models are reviewed in, for example Tsunoda and Fujinami, *J Neuropathol Exp Neurol.* 55:673-686, 1996.

Other models of MS include transgenic animals expressing T cell receptors specific for a myelin protein, e.g., MOG, MBP or PLP. Exemplary models are described, for example, in Bettelli et ai, *JEM* 797:1073-1081, 2003; Illes et al, *Proc. Natl. Acad. Sci. USA,* 101: 11749-11754, 2004; or Rossi et al, *J. Biomolecular Screening,* 12: 481-489, 2007; or are commercially available, e.g., from Jackson Laboratories USA (e.g. mice 2D2 having transgenic T cell receptors reactive with MOG).

Exemplary models of SLE that develop inflammatory neurological symptoms include models or anti-phospholipid syndrome (e.g., as described in Ziporen et ai, *J. Clin, Invest.,* 100: 613-613, 1997) or models reviewed in Brey et ai, *Annals NY Acad Sci.,* 823: 97-106, 1996.

Models of Guillain-Barre syndrome include those caused by sensitization of animals, e.g., rabbits with ganglioside GM1 (e.g., as described in Yuki et al., *Ann Neurol.* 49: 712-720, 2001).

It will be apparent to the skilled artisan from the foregoing that the present disclosure also provides a method for identifying or isolating a cell or a soluble factor for the treatment, prevention or delay of an inflammatory neurological condition, said method comprising:

(i) administering a cell or a soluble factor to a test subject suffering from an inflammatory neurological condition and assessing the inflammatory response or neurological function/dysfunction of the subject;

(ii) comparing the inflammatory response or neurological function/dysfunction of the subject at (i) to the inflammatory response or neurological function/dysfunction of a control subject suffering from the inflammatory neurological condition to which the cell or soluble factor has not been administered, wherein improved inflammatory response or neurological function/dysfunction in the test subject compared to the control subject indicates that the cell or soluble factor treats the inflammatory neurological condition.

The cell may be any cell described herein according to any example.

Cellular Compositions

In one example of the present disclosure STRO-1$^+$ cells and/or progeny cells thereof are administered in the form of a composition. For example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay an inflammatory neurological condition.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

STRO-1$^+$ cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. *J, Ped. Surg.* 23:3-9 1988; Cima, et al. *Biotechnol. Bioeng.* 55:145 1991; Vacanti, et al. *Plast. Reconstr. Surg.* 55:753-9 1991; or synthetic polymers such as polyanhydrides, polyorthoesters, and polylactic acid.

In another example, the cells may be administered in a gel scaffold (such as Gelfoam from Upjohn Company.

The cellular compositions useful for methods described herein may be administered alone or as admixtures with other cells. Cells that may be administered in conjunction with the compositions of the present disclosure include, but are not limited to, other multipotent or pluripotent cells or stem cells, or bone marrow cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of cells. For example, the composition comprises about $1 \times 10^5$ STRO-1$^+$ cells/kg to about $1 \times 10^7$ STRO-1$^+$ cells/kg or about $1 \times 10^6$ STRO-1$^+$ cells/kg to about $5 \times 10^6$ STRO-1$^+$ cells/kg. The exact amount of cells to be administered is dependent upon a variety of factors, including the age, weight, and sex of the patient, and the extent and severity of the inflammatory neurological condition.

In some examples, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors.

In some examples of the disclosure, it may not be necessary or desirable to immunosuppress a patient prior to initiation of therapy with cellular compositions. Accordingly, transplantation with allogeneic, or even xenogeneic, STRO-1$^+$ cells or progeny thereof may be tolerated in some instances.

However, in other instances it may be desirable or appropriate to pharmacologically immunosuppress a patient prior to initiating cell therapy and/or reduce an immune response of a subject against the cellular composition. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. In one example, the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Compositions of Soluble Factors

In one example of the present disclosure, STRO-1$^+$ cell-derived and/or progeny cell-derived supernatant or soluble factors are administered in the form of a composition, e.g., comprising a suitable carrier and/or excipient. For example, the carrier or excipient does not adversely affect the biological effect of the soluble factors or supernatant.

In one example, the composition comprises a composition of matter to stabilize a soluble factor or a component of supernatant, e.g., a protease inhibitor. For example, the protease inhibitor is not included in an amount sufficient to have an adverse effect on a subject.

Compositions comprising STRO-1$^+$ cell-derived and/or progeny cell-derived supernatant or soluble factors may be prepared as appropriate liquid suspensions, e.g., in culture medium or in a stable carrier or a buffer solution, e.g., phosphate buffered saline. Suitable carriers are described herein above. In another example, suspensions comprising STRO-1$^+$ cell-derived and/or progeny cell-derived supernatant or soluble factors are oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the supernatant or soluble factors in the required amount in an appropriate solvent with one or a combination of ingredients described above, as required, followed by filtered sterilization.

Generally, dispersions are prepared by incorporating the supernatant or soluble factors into a sterile vehicle that contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof. In accordance with an alternative aspect of the disclosure, the supernatant or soluble factors may be formulated with one or more additional compounds that enhance its solubility.

Other exemplary carriers or excipients are described, for example, in Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, isotonic agents, for example, sugars, polyalcohols such as mannitol, sorbitol, or sodium chloride are included in the composition. Prolonged absorption of the injectable compositions can be brought about by including in the composition an agent which delays absorption, for example, monostearate salts and gelatin. Moreover, the soluble factors may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The supernatant or soluble factors may be administered in combination with an appropriate matrix, for instance, to provide slow release of the soluble factors.

Additional Components of Compositions

The STRO-1$^+$ cell-derived supernatant or soluble factors, STRO-1$^+$ cells or progeny thereof may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPQXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti¬ platelet receptor antibodies, aspirin, dipyridamole, protamine, hirudin, prostaglandin inhibitors, and platelet inhibitors);

and anti-oxidants (e.g., probucol, vitamin A, ascorbic acid, tocopherol, coenzyme Q-10, glutathione, L-cysteine, N-acetylcysteine) as well as local anesthetics.

In one example, a composition as described herein according to any example comprises an additional factor for the treatment or prophylaxis of an inflammatory neurological condition.

Alternatively, or in addition, cells, secreted factors and/or a composition as described herein according to any example is combined with a known treatment of an inflammatory neurological condition.

In one example, a pharmaceutical composition as described herein according to any example comprises a compound used to treat an inflammatory neurological condition or a symptom thereof. Alternatively, a method of treatment/prophylaxis as described herein according to any example of the disclosure additionally comprises administering a compound used to treat an inflammatory neurological condition or a symptom thereof. Exemplary compounds include a cytotoxic agent, chemotherapeutic agent, immunosuppressive agent, cytokine, cytokine antagonist or antibody, growth factor, hormone, integrin, integrin antagonist or antibody (e.g. an anti-LFA-1 antibody such as efalizumab (RAPTIVA®) commercially available from Genentech, or an anti alpha-4 integrin antibody such as natalizumab (TYSABRI®) available from Biogen Idec/Elan Pharmaceuticals, Inc) etc, or an antibody that binds a B cell surface marker (e.g. anti-CD20 antibody such as rituximab (RITUXAN® OR MABTHERA® or ocrelizumab (both available from Genentech) or ofatumumab (ARZERRA®) available from Genmab/Glaxo Group)).

In some examples of combination therapy, the cells, factors and/or composition is/are combined with an interferon class drug such as IFN-beta-la (REBIF® and AVONEX®) or IFN-beta-1b (BETASERON®); an oligopeptide such a glatiramer acetate (COPAXONE®); a cytotoxic agent such as mitoxantrone (NOVANTRONE®), methotrexate, cyclophosphamide, chlorambucil, azathioprine; intravenous immunoglobulin (gamma globulin); lymphocyte-depleting therapy (e.g., mitoxantrone, cyclophosphamide, Campath, anti-CD4 antibody, cladribine, total body irradiation, bone marrow transplantation); corticosteroid (e.g. methylprednisolone, prednisone, dexamethasone, or glucacorticoid), including systemic corticosteroid therapy; non-lymphocyte-depleting immunosuppressive therapy (e.g., mycophenolate mofetil (MMF) or cyclosporine); cholesterol-lowering drug of the "statin" class, which includes cerivastatin (BAYCOL®), fluvastatin (LESCOL®), atorvastatin (LIPITOR®), lovastatin (MEVACOR®), pravastatin (PRAVACHOL®), Simvastatin (ZOCOR®); estradiol; testosterone (optionally at elevated dosages; Stuve et al *Neurology* 8:290-301, 2002); hormone replacement therapy; treatment for symptoms secondary or related to MS (e.g., spasticity, incontinence, pain, fatigue); disease-modifying anti-rheumatic drug (DMARD); non-steroidal antiinflammatory drug (NSAID); plasmapheresis; levothyroxine; cyclosporin A; somatastatin analog; cytokine or cytokine receptor antagonist; anti-metabolite; immunosuppressive agent; rehabilitative surgery; radioiodine; or a thyroidectomy.

In another example, a composition as described herein according to any example additionally comprises a factor that induces or enhances differentiation of a progenitor cell into a vascular cell. Exemplary factors include, vascular endothelial growth factor (VEGF), platelet derived growth factor (PDGF; e.g., PDGF-BB), and FGF.

In another example, a composition as described herein according to any example additionally comprises a tissue specific committed cell (TSCC). In this respect, International Patent Application No. PCT/AU2005/001445 demonstrates that administration of a TSCC and a STRO-1$^+$ cells can lead to enhanced proliferation of the TSCC. In one example, the TSCC is a neuronal cell, e.g., a neuron, a neuronal progenitor cell or a Schwann cell. Administration of such a composition to a subject may lead to increased production of, for example, neurons or myelin. In another example, the TSCC is a vascular cell. Administration of such a composition to a subject may lead to increased production of vasculature, e.g., leading to increased nutrients being delivered to the affected tissue.

Medical Devices

The present disclosure also provides medical devices for use or when used in a method as described herein according to any example. For example, the present disclosure provides a syringe or catheter or other suitable delivery device comprising STRO-1$^+$ cells and/or progeny cells thereof and/or soluble factors therefrom and/or a composition as described herein according to any example. Optionally, the syringe or catheter is packaged with instructions for use in a method as described herein according to any example.

In another example, the present disclosure provides an implant comprising STRO-1$^+$ cells and/or progeny cells thereof and/or soluble factors therefrom and/or a composition as described herein according to any example. Optionally, the implant is packaged with instructions for use in a method as described herein according to any example. Suitable implants may be formed with a scaffold, e.g., as described herein above and STRO-1$^+$ cells and/or progeny cells thereof and/or soluble factors therefrom.

Modes of Administration

The STRO-1$^+$ cell-derived supernatant or soluble factors, STRO-1$^+$ cells or progeny thereof may be surgically implanted, injected, delivered (e.g., by way of a catheter or syringe), or otherwise administered directly or indirectly to the site in need of repair or augmentation.

In on example, the STRO-1$^+$ cell-derived supernatant or soluble factors, STRO-1$^+$ cells or progeny thereof is/are delivered to the blood stream of a subject. For example, the STRO-1$^+$ cell-derived supernatant or soluble factors, STRO-1$^+$ cells or progeny thereof are delivered parenterally. Exemplary routes of parenteral administration include, but are not limited to, intraperitoneal, intraventricular, intracerebroventricular, intrathecal. In one example, the STRO-1* cell-derived supernatant or soluble factors, STRO-1$^+$ cells or progeny thereof are delivered intra-arterially, into an aorta, into an atrium or ventricle of the heart or into a blood vessel.

In the case of cell delivery to an atrium or ventricle of the heart, cells can be administered to the left atrium or ventricle to avoid complications that may arise from rapid delivery of cells to the lungs.

In one example, the STRO-1$^+$ cell-derived supernatant or soluble factors, STRO-1$^+$ cells or progeny thereof are injected into the site of delivery, e.g., using a syringe or through a catheter or a central line.

Selecting an administration regimen for a therapeutic formulation depends on several factors, including the serum or tissue turnover rate of the entity, the level of symptoms, and the immunogenicity of the entity. For example, an administration regimen maximizes the amount of therapeutic compound delivered to the patient consistent with an acceptable level of side effects. Accordingly, the amount of formulation delivered depends in part on the particular entity and the severity of the condition being treated.

In one example, STRO-1+ cell-derived supernatant or soluble factors, STRO-1+ cells or progeny thereof are delivered as a single bolus dose. Alternatively, STRO-1+ cell-derived supernatant or soluble factors, STRO-1+ cells or progeny thereof are administered by continuous infusion, or by doses at intervals of, e.g., one day, one week, or 1-7 times per week. An exemplary dose protocol is one involving the maximal dose or dose frequency that avoids significant undesirable side effects. A total weekly dose depends on the type and activity of the compound being used. Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects.

In accordance with examples of the disclosure directed to treating or delaying the progression of an inflammatory neurological condition, the STRO-1+ cells and/or progeny cells thereof and/or soluble factors derived therefrom can be administered following diagnosis of the disorder, e.g., using standard methods known in the art and/or described herein.

For those examples directed to preventing or delaying the onset of an inflammatory neurological condition, the STRO-1+ cells and/or progeny cells thereof and/or soluble factors derived therefrom can administered prior to clinical diagnosis of the disorder, e.g., when the subject has suffered from a lesion in myelin however is yet to be diagnosed with MS and/or has produced antiphospholipid antibodies.

The present disclosure is described further in the following non-limiting examples.

EXAMPLES

Example 1: Immunoselection of MPCs by Selection of STRO-3* Cells

Bone marrow (BM) is harvested from healthy normal adult volunteers (20-35 years old). Briefly, 40 ml of BM is aspirated from the posterior iliac crest into lithium-heparin anticoagulant-containing tubes.

BMMNC are prepared by density gradient separation using Lymphoprep™ (Nycomed Pharma, Oslo, Norway) as previously described (Zannettino, A. C. et al. (1998) *Blood* 92: 2613-2628). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia), STRO-3+ (or TNAP+) cells were subsequently isolated by magnetic activated cell sorting as previously described (Gronthos et al. (2003) *Journal of Cell Science* 116: 1827-1835; Gronthos, S. and Simmons, P. J. (1995) *Blood* 85: 929-940). Briefly, approximately $1-3\times10^8$ BMMNC are incubated in blocking buffer, consisting of 10% (v/v) normal rabbit serum in HHF for 20 minutes on ice. The cells are incubated with 200 µl of a ^g/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mn^{2+}$-free PBS supplemented with 1% BSA, 5 mM EDTA and 0.01% sodium azide) as above and resuspended in a final volume of 0.9 ml MACS buffer.

One hundred µï streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International Publication No. WO 2006/108229). After addition of a further. 1 ml MACS buffer, the column is removed from the magnet and the TNAP+ cells are isolated by positive pressure. An aliquot of cells from each fraction can be stained with streptavidin-FITC and the purity assessed by flow cytometry.

Example 2: Cells Selected by STRO-3 mAb are STRO-1$^{bright}$ Cells

Experiments were designed to confirm the potential of using STRO-3 mAb as a single reagent for isolating cells STRO-1$^{bright}$ cells.

Given that STRO-3 (IgG1) is a different isotype to that of STRO-1 (IgM), the ability of STRO-3 to identify clonogenic CFU-F was assessed by two-color FACS analysis based on its co-expression with STRO-1+ cells isolated using the MACS procedure (FIG. 1). The dot plot histogram represents $5\times10^4$ events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1+ cells failed to react with the STRO-3 mAb. Cells isolated by FACS from all four quadrants were subsequently assayed for the incidence of CFU-F (Table 1).

TABLE 1

Enrichment of human bone marrow cells by dual-colour FACS analysis based on the co-expression of the cell surface markers STRO-1 and TNAP (refer to FIG. 1). FACS sorted cells were cultured under standard clonogenic conditions in alpha MEM supplemented with 20% FCS. The data represents the mean number of day 14 colony-forming cells (CFU-F) per $10^5$ cells plated ± SE (n = 3 different bone marrow aspirates). These data suggest that human MPC are exclusively restricted to the TNAP positive fraction of BM which co-express the STRO-1 antigen brightly.

| Bone Marrow Fraction | Frequency of CFU-F/$10^5$ Cells | Enrichment (Fold Increase) |
|---|---|---|
| Unfractionated BMMNC | 11.0 ± 2.2 | 1.0 |
| TNAP+/STRO-1$^{bright}$ | 4,511 ± 185 | 410 |
| TNAP+/STRO-1$^{dull}$ | 0.0 | 0.0 |

Figure 2:
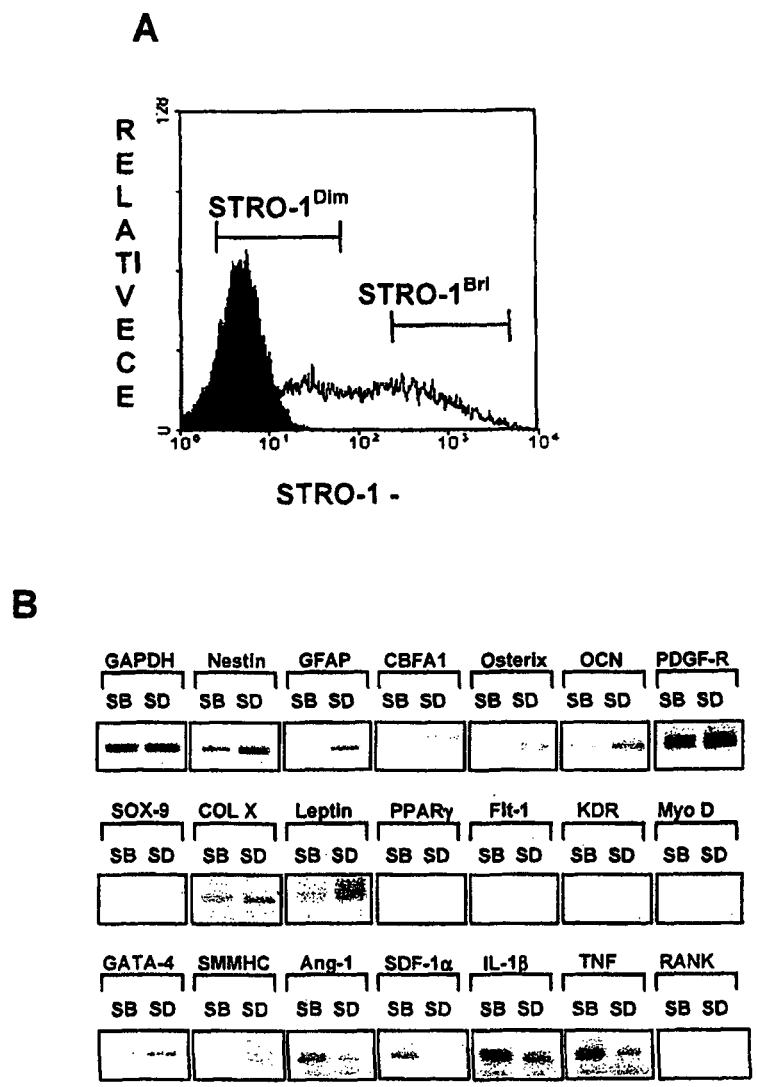
FIG. 2. Gene expression profile of STRO-1$^{bri}$ or STRO-1$^{dim}$ progeny of cultured and expanded STRO-1$^{bri}$ MPC. Single cell suspensions of ex vivo expanded bone marrow MPC were prepared by trypsin/EDTA treatment. Cells were stained with the STRO-1 antibody which was subsequently revealed by incubation with goat-anti murine IgM-fluorescein isothiocyanate. Total cellular RNA was prepared from purified populations of STRO-1$^{dim}$ or STRO-1$^{bri}$ expressing cells, following fluorescence activated cell sorting (A). Using RNAzolB extraction method, and standard procedures, total RNA was isolated from each subpopulation and used as a template for cDNA synthesis. The expression of various transcripts was assessed by PCR amplification, using a standard protocol as described previously (Gronthos et al. *J Cell Sci.* 775:1827-1835, 2003). Primers sets used in this study are shown in Table 2. Following amplification, each reaction mixture was analyzed by 1.5% agarose gel electrophoresis, and visualized by ethidium bromide staining (B). Relative gene expression for each cell marker was assessed with reference to the expression of the housekeeping gene, GAPDH, using ImageQant software (C).
Figure 2:

Example 3: Relative Gene and Surface Protein Expression of STRO-1$^{dull}$ and STRO-1$^{bri}$ Cells In the first series of experiments, semi-quantitative RT-PCR analysis was employed to examine the gene expression profile of various lineage-associated genes expressed by STRO-1$^{dull}$ or STRO-1$^{bri}$ populations, isolated by fluorescence activated cell sorting (FIG. 2A). In the second series of experiments, flow cytometry and mean channel fluorescence analysis was employed to examine the surface protein expression profile of various lineage-associated proteins expressed by STRO-1$^{dull}$ or STRO-1$^{bri}$ populations, isolated by fluorescence activated cell sorting.

Total cellular RNA was prepared from either 2×10$^6$ STRO-1$^{bri}$ or STRO-1$^{dull}$ sorted primary cells, chondrocyte pellets and other induced cultures and lysed using RNAzolB extraction method (Biotecx Lab. Inc., Houston, Tex.), according to the manufacturer's recommendations. RNA isolated from each subpopulation was then used as a template for cDNA synthesis, prepared using a First-strand cDNA synthesis kit (Pharmacia Biotech, Uppsala, Sweden). The expression of various transcripts was assessed by PCR amplification, using a standard protocol as described previously (Gronthos et al., *J. Bone and Min. Res.* 14:48-57, 1999). Primer sets used in this study are shown in Table 2. Following amplification, each reaction mixture was analyzed by 1.5% agarose gel electrophoresis, and visualized by ethidium bromide staining. RNA integrity was assessed by the expression of GAPDH.

Relative gene expression for each cell marker was assessed with reference to the expression of the housekeeping gene, GAPDH, using ImageQant software (FIG. 2B, C). In addition, dual-colour flow cytometric analysis was used to examine the protein expression profile of ex vivo expanded MPC based on their expression of a wider range of cell lineage-associated markers in combination with the STRO-1 antibody. A summary of the general phenotype based on the gene and protein expression of STRO-1$^{dull}$ and STRO-1$^{bri}$ cultured cells is presented in Table 3. The data indicate that ex vivo expanded STRO-1$^{bri}$ MPC exhibit differentially higher expression of markers associated with perivascular cells, including angiopoietin-1, VCAM-1, SDF-1, IL-1$_\beta$, TNF$\alpha$, and RANKL. Comparisons between the protein and gene expression profiles of STRO-1$^{dull}$ and STRO-1$^{bri}$ cultured cells are summarized in Tables 3 and 4.

Subtractive hybridization studies were also performed in order to identify genes uniquely expressed by STRO-1$^{bri}$ cells. Briefly, STRO-1$^{dull}$ and STRO-1$^{bri}$ were isolated as described above (see FIG. 3A). Total RNA was prepared from STRO-1$^{dull}$ and STRO-1$^{bri}$ cells pooled from 5 different marrow samples using the RNA STAT-60 system (TEL-TEST). First-strand synthesize was performed using the SMART cDNA synthesis kit (Clontech Laboratories). The resultant mRNA/single-stranded cDNA hybrid was amplified by long-distance PCR (Advantage 2 PCR kit; Clontech) using specific primer sites at the 3' and 5' prime ends formed during the initial RT process according to the manufacturer's specifications. Following RsaI digestion of the STRO-1bright cDNA, 2 aliquots were used to ligate different specific adaptor oligonucleotides using the Clontech PCR-Select cDNA Subtraction Kit. Two rounds of subtractive hybridization were performed using STRO-1$^{bri}$ (tester) and STRO-1$^{dull}$ (driver) cDNA, and vice versa, according to the manufacturer's protocol. This procedure was also performed in reverse using STRO-1$^{dull}$ tester cDNA hybridized against STRO-1$^{bri}$ driver cDNA.

Figure 3:
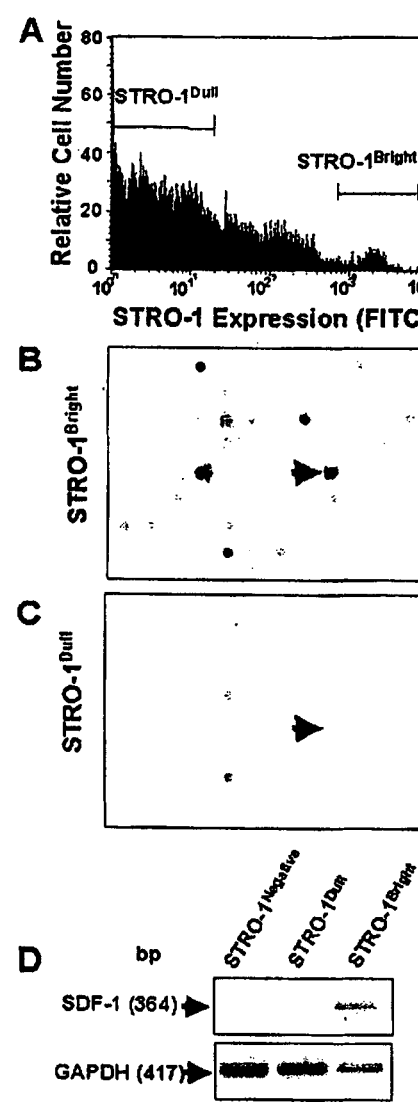
FIG. 3. STRO-1$^{bri}$ progeny of cultured and expanded STRO-1+ MPC express high levels of SDF-1, STRO-1$^{dim}$ progeny do not. (A) MACS-isolated preparations of STRO-1+ BMMNCs were partitioned into different STRO-1 subsets according to the regions, STRO-1$^{bright}$ and STRO-1$^{dim/dull}$ using FACS. Total RNA was prepared from each STRO-1 subpopulation and used to construct a STRO-1$^{bright}$ subtraction hybridization library (B-C). Replicate nitrocellulose filters, which have been blotted with representative PCR products amplified from bacterial clones transformed with STRO-1$^{bright}$ subtracted cDNA. The filters were then probed with either [$^{32}$P] deoxycytidine triphosphate (dCTP>-labeled STRO-1$^{bright}$ (B) or STRO-1$^{dim/dull}$n (C) subtracted cDNA. The arrows indicate differential expression of 1 clone containing a cDNA fragment corresponding to human SDF-1. (D) Reverse transcriptase (RT)-PCR analysis demonstrating the relative expression of SDF-1 and glyceraldehyde-3-phosphate dehydrogenase (GAPDH) transcripts in total RNA prepared from freshly MACS/FACS-isolated BMMNC STRO-1 populations prior to culture. bp indicates base pair.

To identify genes uniquely expressed by STRO-1$^{bri}$ population, STRO-1$^{bri}$-subtracted cDNA was used to construct replicate low-density microarray filters comprising 200 randomly selected bacterial clones transformed with the STRO-1$^{bri}$ subtracted cDNAs ligated into a T/A cloning vector. The microarrays were subsequently probed with either [$^{32}$P] dCTP-labeled STRO-1$^{bri}$ or STRO-1$^{dull}$ subtracted cDNA (FIG. 3B-C). Differential screening identified a total of 44 clones, which were highly differentially expressed between the STRO-1$^{dull}$ and STRO-1$^{bright}$ subpopulations. DNA sequencing of all the differentially expressed clones revealed that only 1 clone was representative of a known stromal cell mitogen; namely, platelet-derived growth factor (PDGF) (Gronthos and Simmons, *Blood.* 85: 929-940, 1995). Interestingly, 6 of the 44 clones were found to contain DNA inserts corresponding to the chemokine, stromal-derived factor-1 (SDF-1). The high abundance of SDF-1 transcripts in human STRO-1$^{bright}$ cells was confirmed by semiquantitative RT-PCR of total RNA prepared from freshly sorted STRO-1$^{bright}$, STRO-1$^{dull}$, and STRO-1$^{negative}$ bone marrow subpopulations (FIG. 3D and Table 3).

TABLE 2

RT-PCR primers and conditions for the specific amplification of human mRNA

| Target Gene | Sense/Antisense (5'-3') Primer Sequences | Product Size |
|---|---|---|
| GAPDH | CACTGACACGTTGGCAGTGG (SEQ ID NO: 1) CATGGAGAAGGCTGGGGCTC (SEQ ID NO: 2) | 417 |
| SDF-1 | GAGACCCGCGCTCGTCCGCC (SEQ ID NO: 3) GCTGGACTCCTACTGTAAGG G (SEQ ID NO: 4) | 364 |
| IL-Iβ | AGGAAGATGCTGGTTCCCTC TC (SEQ ID NO: 5) CAGTTCAGTGATCGTACAGG TGC (SEQ ID NO: 6) | 151 |
| FLT-1 | TCACTATGGAAGATCTGATT TCTTACAGT (SEQ ID NO: 7) GGTATAAATACACATGTGCT TCTAG (SEQ ID NO: 8) | 380 |
| TNF-α | TCAGATCATCTTCTCGAACC (SEQ ID NO: 9) CAGATAGATGGGCTCATACC (SEQ ID NO: 10) | 361 |
| KDR | TATAGATGGTGTAACCCGGA (SEQ ID NO: 11) TTTGTCACTGAGACAGCTTG G (SEQ ID NO: 12) | 450 |
| RANKL | AACAGGCCTTTCAAGGAGCT G (SEQ ID NO: 13) TAAGGAGGGGTTGGAGACCT CG (SEQ ID NO: 14) | 538 |
| Leptin | ATGCATTGGGAACCCTGTGC (SEQ ID NO: 15) GCACCCAGGGCTGAGGTCCA (SEQ ID NO: 16) | 492 |
| CBFA-1 | GTGGACGAGGCAAGAGTTTC A (SEQ ID NO: 17) TGGCAGGTAGGTGTGGTAGT G (SEQ ID NO: 18) | 632 |
| PPARγ2 | AACTGCGGGGAAACTTGGGA GATTCTCC (SEQ ID NO: 18) AATAATAAGGTGGAGATGCA GGCTCC (SEQ ID NO: 19) | 341 |
| OCN | ATGAGAGCCCTCACACTCCT C (SEQ ID NO: 20) CGTAGAAGCGCCGATAGGC (SEQ ID NO: 21) | 289 |
| MyoD | AAGCGCCATCTCTTGAGGTA (SEQ ID NO: 22) GCGAGAAACGTGAACCTAGC (SEQ ID NO: 23) | 270 |

TABLE 2-continued

RT-PCR primers and conditions for the specific amplification of human mRNA

| Target Gene | Sense/Antisense (5'-3') Primer Sequences | Product Size |
|---|---|---|
| SMMHC | CTGGGCAACGTAGTAAAACC (SEQ ID NO: 24) TATAGCTCATTGCAGCCTCG (SEQ ID NO: 25) | 150 |
| GFAP | CTGTTGCCAGAGATGGAGGT T (SEQ ID NO: 26) TCATCGCTCAGGAGGTCCTT (SEQ ID NO: 27) | 370 |
| Nestin | GGCAGCGTTGGAACAGAGGT TGGA (SEQ ID NO: 28) CTCTAAACTGGAGTGGTCAG GGCT (SEQ ID NO: 29) | 460 |
| SOX9 | CTCTGCCTGTTTGGACTTTG T (SEQ ID NO: 30) CCTTTGCTTGCCTTTTACCT C (SEQ ID NO: 31) | 598 |
| Collagen type X | AGCCAGGGTTGCCAGGACCA (SEQ ID NO: 32) TTTTCCCACTCCAGGAGGGC (SEQ ID NO: 33) | 387 |
| Aggrecan | CACTGTTACCGCCACTTCCC (SEQ ID NO: 34) ACCAGCGGAAGTCCCCTTCG (SEQ ID NO: 35) | 184 |

TABLE 3

Summary of the Relative Gene Expression in STRO-1$^{Bri}$ and STRO-1$^{Dull}$ populations. A list of genes which displayed measurable and differential expression between the STRO-1$^{Bri}$ and STRO-1$^{Dull}$ populations as determined by reverse transcription-PCR are presented. Values represent the relative gene expression with reference to the house-keeping gene, GAPDH.

| | | Gene Expression relative to GAPDH | |
|---|---|---|---|
| Tissue | Marker | STRO-1$^{Bri}$ | STRO-1$^{Dull}$ |
| Neurons | GFAP (Glial Fibrillary Acidic Protein) | 0.1 | 0.7 |
| Bone | OCN (Osteocalcin) | 1.1 | 2.5 |
| | OSX (Osterix) | 0.4 | 1.3 |
| | CBFA-1 (Core Factor Binding Protein-1) | 0.3 | 0.6 |
| Immunoregulatory | RANKL (Receptor Activator of Nuclear Factor κ B) | 1.6 | 0.3 |
| | SDF-1-alpha (Stromal Derived factor-1-alpha) | 3.2 | 0.1 |
| Fat | Leptin | 3.1 | 4.2 |
| Cardiomyocytes | GATA-4 | 1.1 | 2.9 |
| Endothelial cells | Ang-1 (Angiopoietin-1) | 1.5 | 0.8 |
| Chondrocytes | Sox 9 | 0.3 | 1.1 |
| | COL X (Collagen X) | 3.5 | 2.8 |
| Pro-inflammatory Cytokines | TNF-alpha (Tumor necrosis alpha) | 1.7 | 0.9 |

To correlate protein surface expression with density of STRO-1 expression, single cell suspensions of ex vivo expanded cells derived bone marrow MPC were prepared by trypsin/EDTA detachment and subsequently incubated with the STRO-1 antibody in combination with antibodies identifying a wide range of cell lineage-associated markers. STRO-1 was identified using a goat anti-murine IgM-fluorescein isothiocyanate while all other markers were identified using either a goat anti-mouse or anti-rabbit IgG-phycoerythrin. For those antibodies identifying intracellular antigens, cell preparations were first labeled with the STRO-1 antibody, fixed with cold 70% ethanol to permeabilize the cellular membrane and then incubated with intracellular antigen-specific antibodies. Isotype matched control antibodies were used under identical conditions. Dual-colour flow cytometric analysis was performed using a COULTER EPICS flow cytometer and list mode data collected. The dot plots represent 5,000 listmode events indicating the level of fluorescence intensity for each lineage cell marker (y-axis) and STRO-1 (x-axis). The vertical and horizontal quadrants were established with reference to the isotype matched negative control antibodies.

TABLE 4

Summary of the Relative Protein Expression in STRO-1$^{Bri}$ and STRO-1$^{Dull}$ populations. A list of proteins which displayed differential expression between the STRO-1$^{Bri}$ and STRO-1$^{Dull}$ populations as determined by flow cytometry are presented. Values represent the relative mean fluorescence intensity of staining.

| | | Mean Fluorescence Intensity | |
|---|---|---|---|
| Tissue | Marker | STRO-1$^{Bri}$ | STRO-1$^{Dull}$ |
| Neurons | Neurofilament | 1.7 | 20.5 |
| Bone | ALK PHOS (Alkaline Phophatase) | 5.7 | 44.5 |
| Immunoregulatory | RANKL (Receptor Activator of Nuclear Factor κ B) | 658.5 | 31.0 |
| Epithelial Cells | CytoKeratin 10 + 13 | 1.2 | 23.3 |
| | Cytokeratin 14 | 1.8 | 8.8 |
| Smooth Muscle | α-SMA (Alpha Smooth Muscle Actin) | 318.0 | 286.0 |
| Chondrocytes | Byglycan | 84.4 | 65.9 |
| Basal Fibroblast | Tenascin C | 22.2 | 6.9 |
| Cardiomyocyte | Troponin C | 2.5 | 15.0 |

These results show that SDF-1 alpha and RANKL are highly expressed by STRO-1$^{bri}$ cells. This is important because both of these proteins are known to be involved in up-regulation of CD4$^+$ CD25$^+$ regulatory T (Treg) cells which confer protection against immune disorders such as EAE (Loser et al, Nature Medicine 12:1372-1379, 2006; Hess, Biol. Blood Marrow Transplant, 12 (1 Suppl 2): 13-21, 2006; and Meiron et al, J. Exp. Medicine 205:2643-2655, 2008).

Example 4: Effect of STRO-1$^+$ Cells in EAE

For the following experiments the myelin oligodendrocyte glycoprotein (MOG)-induced experimental inflammatory encephalomyelitis (EAE) in C57Bl/6J mice was used. C57Bl/6J mice display similar phenotypic symptoms (progressive paralysis) to that of MS patients as well as showing extensive inflammation, demyelination and axonal loss/damage in the CNS. The immunization procedure for the induction of EAE, assessment of clinical symptoms and MPC transplantation used is as follows.

Active Induction of EAE

Mice were immunized with 200 μg recombinant MOG dissolved in Phosphate Buffered Saline (PBS) and mixed with an equal volume of Freund's complete adjuvant containing 400 μg of killed *Mycobacterium tuberculosis* H37Ra. 0.1 ml of this mixture was injected subcutaneously into the right and left flank (total 0.2 ml/mouse) using a 25 gauge (G) needle. Mice were also immunized with 350 ng inactivated

*Bordetella pertussis* toxin in 0.30 ml of PBS intravenously (i.v.) via tail vein of on day 0 and day 2 using a 29 G needle. Gentle pressure was applied to the I.V. site for 30 sec after the injection to reduce the risk of bleeding from the i.v. site.

Mice were monitored every 2-5 minutes for 10-15 minutes to ensure there is no active bleeding.

Treatment with MPCs

MPCs were isolated essentially as described in Example 1. On days 8, 10 and 12 after disease induction, $2 \times 10^5$ or $4 \times 10^5$ MPCs were administered as a single intravenous (i.v.) injection in a volume of 200 μl PBS (see Table 5). Controls received i.v. injections of equal volumes of PBS only. Mice were monitored daily and clinical signs scored according to the scale described below. Experiments were continued for approximately 36 days to monitor the course of disease. At termination of the experiment, brain, spinal cord and optic nerve were dissected and fixed in formalin solution.

TABLE 5

Summary of Treatment Regimen

| Treatment | No of cells per mouse per injection | Total MPC injected per 20 g mouse | Number of mice |
|---|---|---|---|
| PBS I.V. | — | — | 12 |
| High dose MPC I.V. | $4 \times 10^5$ MPC | $6 \times 10^6$ MPC/Kg | 5 |
| Low dose MPC I.V. | $2 \times 10^5$ MPC | $3 \times 10^6$ MPC/Kg | 5 |

Monitoring of Mice

All mice were examined daily for signs of neurological dysfunction for the entirety of the experiment.

Grading of neurological dysfunction:
0—normal
1—loss of tail tone only
2—mild weakness of 1 or 2 hind limbs and abnormal gait
3—inability to move hind limbs
4—inability to move hind limbs and mild forelimb weakness
5—dead Results Control C57Bl/6J mice display similar phenotypic symptoms (progressive paralysis) to that of MS patients as well as showing extensive inflammation, demyelination and axonal loss/damage in the CNS.

Figure 4:
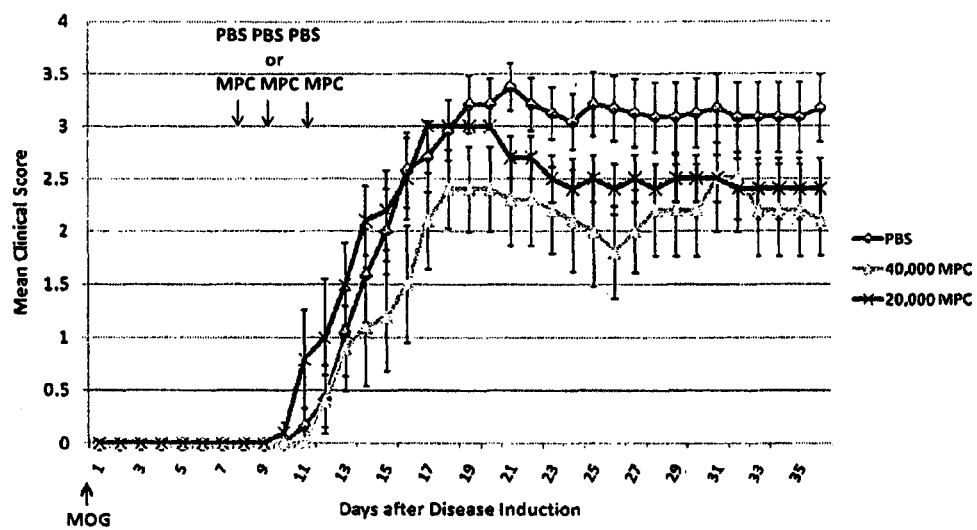
FIG. 4 is a graphical representation showing the effect of MPC treatment on mean clinical disease scores in a model of chronic progressive EAE. C57BL/6 Mice were immunised with MOG35-55 on day 0 and then treated with intravenous injections of MPCs on days 8, 10 and 12 after disease induction. The dosage of MPCs is indicated.

As shown in FIG. 4, intravenously administered MPCs administered at the onset of EAE disease induction are able to inhibit the severity of the mean clinical disease scores over the course of 36 days compared to EAE animals treated with PBS.

Figure 5:
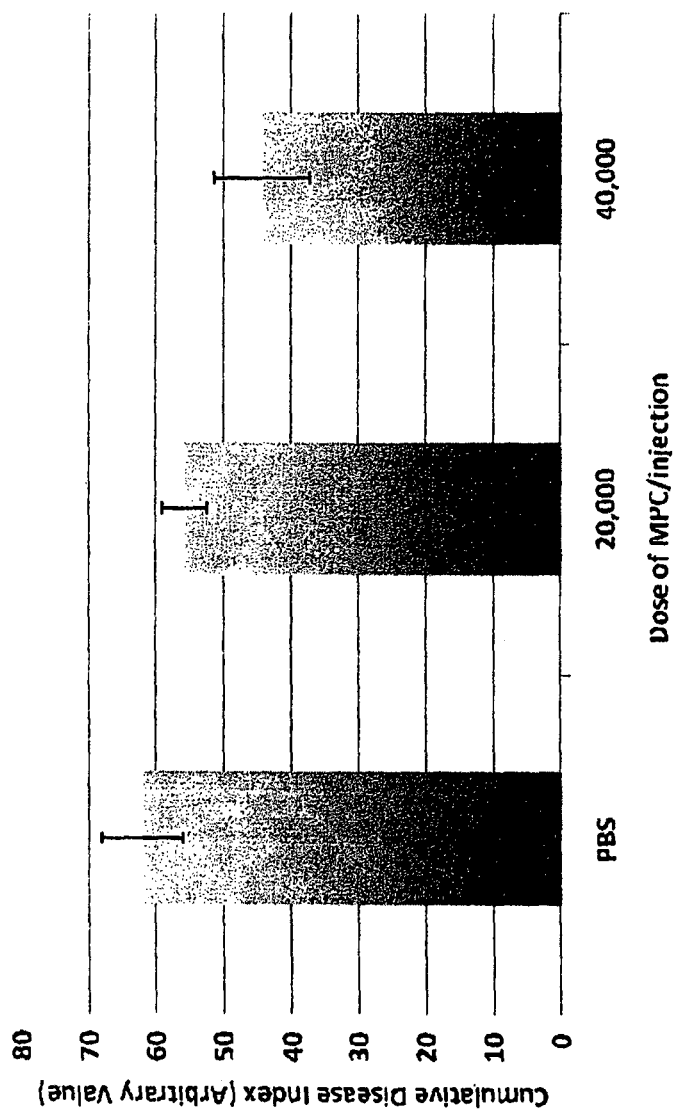
FIG. 5 is a graphical representation showing that MPC treatment induces dose-dependent reduction in cumulative disease index in chronic progressive EAE (total area under the curve analysis of mean clinical disease score)

FIG. 5 shows that MPC treatment induces a dose-dependent reduction in cumulative disease index in chronic progressive EAE (total area under the curve analysis of mean clinical disease score).

The effects of administration of the MPCs are summarized in Table 6:

TABLE 6

Summary of clinical outcome in mouse EAE model following treatment with MPCs

| | PBS | Total MPC dose $0.6 \times 10^5$ ($3 \times 10^6$ MPC/kg) | Total MPC dose $1.2 \times 10^5$ ($6 \times 10^6$ MPC/kg) |
|---|---|---|---|
| Disease incidence | 12/12 | 5/5 | 5/5 |
| Day disease onset (range) | 13.92 ± 0.54 (11-18) | 11.6 ± 0.6 (10-13) | 13.8 ± 0.97 (12-17) |
| Death or severe disease (%) | 3/12 (25) | 0/5 (0) | 0/5 (0) |
| Maximum clinical score | 3.5 ± 0.26 | 3 | 2.6 ± 0.4 |
| Cumulative disease index (Area under curve) | 62 ± 5.8 | 55.7 ± 2.1 | 44.3 ± 4.4 |

Data in Table 6 show that all animals demonstrate neurological disease between 10-18 days following induction of EAE with MOG peptide 35-55. 25% (3/12) of control animals treated with PBS died in comparison to 0/15 animals treated with MPC The maximum clinical score was the highest in the control group and all MPC treated groups showed a lower maximal clinical score The cumulative disease index which is the area under the curve (AUC) for the mean clinical score for the duration of 36 days were all lower for the MPC therapy groups compared to that observed for the control group indicating a robust and sustained EAE disease suppression by MPC.

These data show that in this model of a human inflammatory neurological condition human MPCs are effective in reducing the clinical severity of EAE.

Example 4: Effect of MPCs on T Cell Proliferation

MPC-treated mice and controls as described in Example 3 were culled on day 36 after disease induction (MOG35-55 immunization). Splenocytes were cultured in vitro with media alone or re-stimulated with MOG35.55 and then T-cell proliferative responses were measured through [$^3$H]-thymidine incorporation. The specific proliferative responses to MOG were compared to the matched splenocytes cultured in media-alone (unstimulated). Splenocytes cultured in PMA/Ionomycin served to determine the non-specific (antigen-independent) stimulation of T cell proliferation.

Figure 6:
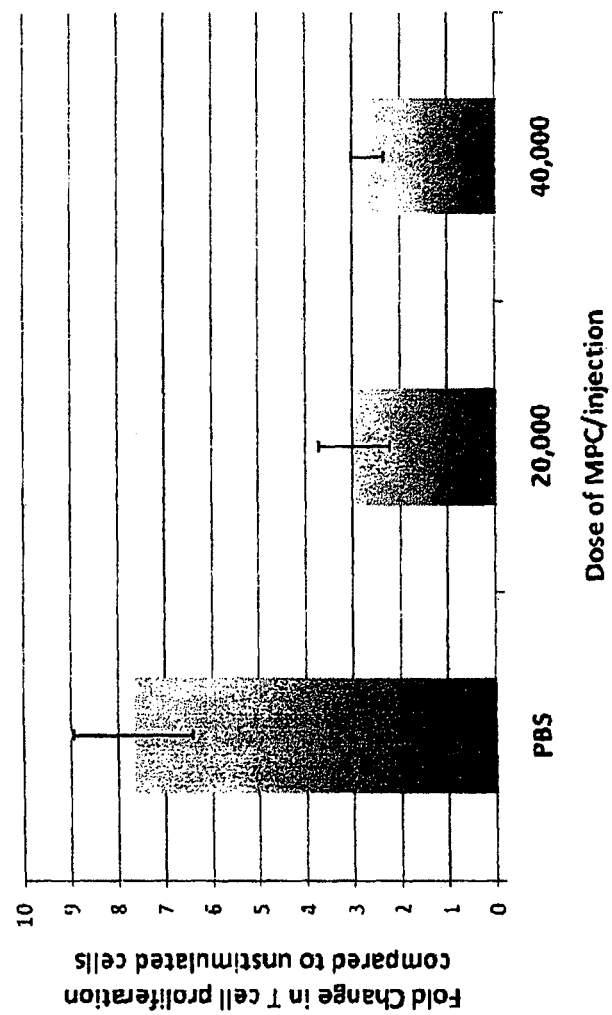
FIG. 6 is a graphical representation showing the fold change in proliferation of splenocytes isolated from mice immunized with MOG35.55 compared to unstimulated splenocytes following stimulation with MOG35.55.
Figure 7:
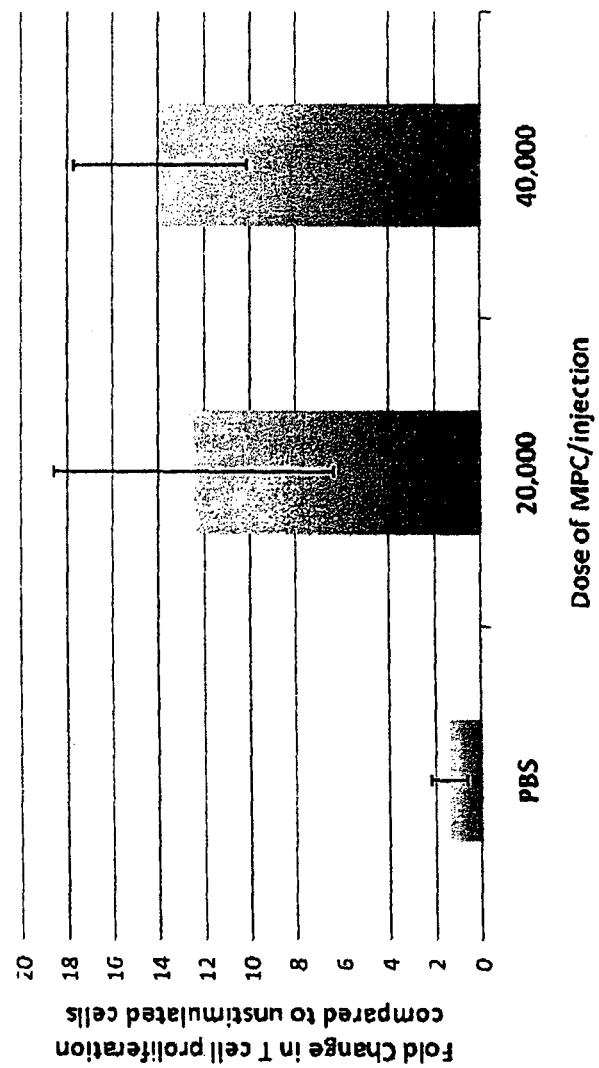
FIG. 7 is a graphical representation showing the fold change in proliferation of splenocytes isolated from mice immunized with MOG35.55 compared to unstimulated splenocytes following non-specific restimulation with PMA/ionomycin.

Data presented in FIG. 6 demonstrate that T cell immune responses to secondary in vitro antigenic challenge with MOG are inhibited in comparison to T cells cultured from control animals. Data in FIG. 7 show that T cell immune responses in animals previously treated with MPC in vivo maintain potent responses to non-specific stimulation with PMA/ionomycin in vitro in comparison to T cells cultured from PBS-treated control animals. This exaggerated response to non-specific stimulation may reflect the xenogenic response to human antigens by mouse T-cells.

These data show that human MPCs reduce or prevent T cell immune response to a specific antigen (e.g., antigenic stimulation by MOG), even 24 days after the last administration of MPCs. The data indicate that STRO-1. enriched MPC induce tolerance to multiple sclerosis antigens.

Example 6: In Vitro Effects of MPCs

The immunoregulatory properties of MPC are tested by proliferation assays, mixed lymphocyte reactions and cytokines production as described below.

Proliferation Assays and Mixed Lymphocyte Reactions

Mononuclear cells are collected from the spleens of healthy C57BL/6 mice, 2D2 transgenic mice or MOG-immunized mice treated with MPCs or vehicle alone essentially as described in Example 4. Single cell suspensions are prepared in complete RPMI media containing 10% FBS, 2 mM L-glutamine, 100 units/ml penicillin, 100 μg/ml streptomycin (all from Invitrogen), 1 mM sodium pyruvate (Sigma) and 50 μM β-mercaptoethanol (Sigma). Following red blood cell lysis, cells are washed twice and then seeded in 96-well flat bottom microtiter plates (Nunc) in triplicate at a concentration of $2.5 \times 10^5$ cells per well in the presence of either 20 μg/ml $MOG_{35-55}$ (GL Biochem), 800 ng/ml ionomycin and 20 pg/ml phorbol myristate acetate (PMA) (both from Sigma), or into wells pre-coated with 10 μg/ml anti-CD3 and 10 μg/ml anti-CD8 (both from BD). Cells are then incubated at 37° C. with 5% $CO_2$ for 72 hours and 1 μCi/well [3H] thymidine is added during the last 18 hours of culture. Cells are harvested onto filter mats and incorporated radioactive nucleic acids counted on a Top Count Harvester (Packard Biosciences). For experiments involving inhibition of T-cell proliferation by MPC, concentrations of MPC ranging from 2.5 to $0.002 \times 10^4$ cells per well are seeded prior to the addition of splenocytes.

In mixed lymphocyte reactions (MLR), $2 \times 10^5$ splenocytes from C57BL/6 mice (responders) are incubated with equal numbers of irradiated (20 Gy) Balb/c stimulators or irradiated MPC and cultured for a period of 5 days, with the addition of 1 μCi/well [3H] thymidine during the last 24 hours of culture.

In MLRs involving T-cell inhibition, $2 \times 10^4$ irradiated MPC are seeded into the wells prior to the addition of splenocytes.

Cytokine Production

Supernatants used for analysis of cytokine production are obtained from two day co-cultures of $2.5 \times 10^6$ splenocytes from 2D2 transgenic mice stimulated with 20 μg/ml MOG35.55 alone or in the presence of $2 \times 10^4$ MPC (MPC:splenocyte ratio of 1:10). Quantitative analysis of cytokines us performed using a mouse Th1/Th2/Th17 cytometric bead array (CBA) kit (BD) essentially according to the manufacturer's instructions and analyzed on a BD FACSCanto II flow cytometer. The following cytokines are measured: interleukin (IL)-2, IL-4, IL-6, IL-10, IL-17A, interferon-γ (IFN-γ) and tumor necrosis factor-a (TNF-a).

The invention claimed is:

1. A method for treating a subject with multiple sclerosis, the method comprising administering to the subject a population of cells enriched for STRO-1$^+$ TNAP$^+$ multipotential cells in an amount effective to treat the subject.

2. The method of claim 1, wherein the multiple sclerosis is associated with, or caused by, a T cell response to an inflammatory stimulus.

3. The method of claim 1, wherein the multiple sclerosis is a chronic progressive form of multiple sclerosis or a relapsing-remitting form of multiple sclerosis.

4. The method of claim 1, wherein the population enriched for STRO-1$^+$ TNAP$^+$ multipotential cells is administered systemically.

5. The method of claim 1, comprising:
 (i) administering an amount of the population enriched for STRO-1$^+$ TNAP$^+$ multipotential cells effective to increase the number of regulatory T (Treg) cells in the subject and/or at the site of pathogenesis of the disease;
 (ii) administering between $2 \times 10^6$ and $8 \times 10^6$ STRO-1$^+$ TNAP$^+$ multipotential cells per kg;
 (iii) administering between $3 \times 10^6$ and $6 \times 10^6$ STRO-1$^+$ TNAP$^+$ multipotential cells per kg; or
 (iv) administering a low dose of STRO-1$^+$ TNAP$^+$ multipotential cells,
 wherein the low dose of STRO-1$^+$ TNAP$^+$ cells comprises between $0.1 \times 10^6$ and $3 \times 10^6$ STRO-1$^+$ cells per kg or comprises about $3 \times 10^6$ STRO-1$^+$ TNAP$^+$ cells.

6. The method of claim 1, wherein the population enriched for STRO-1$^+$ TNAP$^+$ multipotential cells is administered once weekly or is administered once every four weeks.

7. The method of claim 1, wherein the population enriched for STRO-1$^+$ TNAP$^+$ multipotential cells is autogeneic or allogeneic.

8. The method of claim 1, wherein the population enriched for STRO-1$^+$ TNAP$^+$ multipotential cells has been culture expanded prior to administration.

9. A method for treating a subject with multiple sclerosis, the method comprising administering to the subject a population of cells enriched for STRO-1$^+$ TNAP$^+$ multipotential cells such that at least 5% of the cells are STRO-1$^+$ TNAP$^+$ multipotential cells so as to treat the subject.

* * * * *